(12) United States Patent
Fujii et al.

(10) Patent No.: US 10,881,294 B2
(45) Date of Patent: Jan. 5, 2021

(54) OPHTHALMIC APPARATUS

(71) Applicant: TOPCON CORPORATION, Tokyo (JP)

(72) Inventors: Kouta Fujii, Saitama (JP); Makoto Saika, Tokyo (JP); Jun Sakai, Saitama (JP)

(73) Assignee: TOPCON CORPORATION, Tokyo (JP)

( * ) Notice: Subject to any disclaimer, the term of this patent is extended or adjusted under 35 U.S.C. 154(b) by 149 days.

(21) Appl. No.: 16/132,507

(22) Filed: Sep. 17, 2018

(65) Prior Publication Data
US 2019/0082957 A1    Mar. 21, 2019

(30) Foreign Application Priority Data

Sep. 21, 2017  (JP) ................. 2017-180803

(51) Int. Cl.
*A61B 3/10* (2006.01)
*A61B 3/12* (2006.01)
(Continued)

(52) U.S. Cl.
CPC .............. *A61B 3/12* (2013.01); *A61B 3/0025* (2013.01); *A61B 3/102* (2013.01); *A61B 3/0058* (2013.01); *A61B 3/1005* (2013.01); *A61B 3/14* (2013.01)

(58) Field of Classification Search
CPC ......... A61B 3/102; A61B 3/1005; A61B 3/14; A61B 3/12; A61B 3/0025; A61B 3/1225; A61B 5/0066; G01B 9/02091
See application file for complete search history.

(56) References Cited

U.S. PATENT DOCUMENTS 7,828,437 B2   11/2010  Kikawa et al.
7,980,697 B2    7/2011  Tsukada et al.
(Continued)

FOREIGN PATENT DOCUMENTS

EP    1972265 A2    9/2008
EP    2404545 A2    1/2012
(Continued)

OTHER PUBLICATIONS

Extended European Search Report dated Feb. 15, 2019 in European Application No. 18194502.3-1124.

*Primary Examiner* — Christopher Stanford
(74) *Attorney, Agent, or Firm* — Xsensus LLP

(57) ABSTRACT

An ophthalmic apparatus of an embodiment include a data acquisition device, distribution data generator, correction value calculator, magnification corrector, and data comparator. The data acquisition device acquires three dimensional data by applying OCT to the fundus of a subject's eye. The distribution data generator generates distribution data of a predetermined measurement value in the fundus based on the three dimensional data. The correction value calculator calculates a magnification correction value based on a predetermined condition for acquiring the three dimensional data. The magnification corrector changes at least one of the size of standard distribution data generated in advance for the predetermined measurement value and the size of the distribution data, based on the magnification correction value. The data comparator compares the distribution data with the standard distribution data, at least one of whose sizes has been changed by the magnification corrector.

10 Claims, 15 Drawing Sheets

(51) Int. Cl.
*A61B 3/00* (2006.01)
*A61B 3/14* (2006.01)

(56) References Cited

U.S. PATENT DOCUMENTS

| | | | | |
|---|---|---|---|---|
| 9,980,643 | B2* | 5/2018 | Fujimura | A61B 3/154 |
| 2006/0087615 | A1 | 4/2006 | Kojima et al. | |
| 2007/0236660 | A1* | 10/2007 | Fukuma | A61B 3/102 |
| | | | | 351/205 |
| 2007/0236661 | A1* | 10/2007 | Fukuma | A61B 3/102 |
| | | | | 351/205 |
| 2009/0030299 | A1 | 1/2009 | Naito et al. | |
| 2009/0190092 | A1 | 7/2009 | Tsukada et al. | |
| 2011/0267583 | A1* | 11/2011 | Hayashi | G01B 9/02028 |
| | | | | 351/206 |
| 2012/0002164 | A1 | 1/2012 | Yamamoto et al. | |
| 2014/0205169 | A1 | 7/2014 | Yamakawa et al. | |
| 2016/0302659 | A1 | 10/2016 | Boss et al. | |
| 2016/0302664 | A1 | 10/2016 | Yamakawa et al. | |
| 2017/0135578 | A1* | 5/2017 | Nakagawa | A61B 3/0041 |

FOREIGN PATENT DOCUMENTS

| | | | |
|---|---|---|---|
| EP | 3081146 | A1 | 10/2016 |
| EP | 3127473 | A1 | 2/2017 |
| JP | 08-206081 | A | 8/1996 |
| JP | H10-179517 | A | 7/1998 |
| JP | 2006-122160 | A | 5/2006 |
| JP | 2008-206684 | A | 9/2008 |
| JP | 2008-237237 | A | 10/2008 |
| JP | 2009-000354 | A | 1/2009 |
| JP | 2009-028287 | A | 2/2009 |
| JP | 2013-248376 | A | 12/2013 |
| JP | 2016-043155 | A | 4/2016 |
| JP | 2016077774 | A * | 5/2016 ............ A61B 3/1005 |

\* cited by examiner

OPHTHALMIC APPARATUS

CROSS-REFERENCE TO RELATED APPLICATION

This application is based upon and claims the benefit of priority from Japanese Patent Application No. 2017-180803, filed Sep. 21, 2017; the entire contents of which are incorporated herein by reference.

FIELD

Embodiments described herein relate to an ophthalmic apparatus.

BACKGROUND

Importance of diagnostic imaging and image analysis is increasing in ophthalmic examinations. In particular, the application of optical coherence tomography (OCT) to ophthalmology is spurring this trend. The OCT enables three dimensional imaging, three dimensional structural analysis and functional analysis of a subject's eye, and serves an effective role for acquiring distribution of various measurement values, for example. Distribution of the thickness of a layer tissue of eye fundus is an example of the distribution of the measurement values. The layer thickness distribution acquired for the subject's eye is compared with data of normal eyes (healthy eyes, healthy-seeming eyes) in order to determine the presence or absence of a disease. The normal eye data is referred to as normative data.

The accuracy of fundus structural analysis such as layer thickness distribution analysis is influenced by a magnification error caused by the subject's eye. For example, normative data comparative analysis addresses layer thickness distribution in a predetermined area of an eye fundus. As a specific example, glaucoma diagnosis deals with thickness distribution of a layer (e.g., nerve fiber layer, ganglion cell layer) in a predetermined area around the optic nerve head and thickness distribution of a layer (e.g., nerve fiber layer, ganglion cell layer) in a predetermined area including the fovea centralis. Here, the predetermined areas have preset sizes. A typical size of the areas are 6 mm×6 mm or 9 mm×9 mm.

In order to favorably perform such analysis, it is necessary to apply OCT scan to the predetermined area of an eye fundus. However, even if OCT scan is performed under a fixed scan condition, the area in the eye fundus actually scanned varies depending on the axial length and the refractive power (diopter) of the subject's eye.

For example, as shown in FIG. 1, when OCT measurement light is incident at the fixed angle $\theta$ on the subject's eye E1 with the axial length L1 and on the subject's eye E2 with the axial length L2 (>L1), the height Y2 of the projection position of the measurement light on the fundus of the subject's eye E2 is larger than the height Y1 of the projection position of the measurement light on the fundus of the subject's eye E1 (Y2>Y1). As understood from this, the longer the axial length is, the larger the height of the projection position of the measurement light on the fundus becomes. The size of OCT scan is defined by the maximum deflection angle of measurement light. Therefore, even if the size condition of OCT scan is fixed, the area in eye fundus actually scanned changes according to axial length values. The same is true for diopters of subject's eyes.

In normative data comparative analysis, normative data for a predetermined area of eye fundus (i.e., for an area of a predetermined size) is prepared. The normative data is, for example, data in which standard values of layer thickness of normal eyes are respectively assigned to a plurality of regions obtained by dividing the predetermined area of funduses of standard eyes. Here, each of the standard values of the layer thickness of the normal eyes is, for example, an average value in the corresponding region. Such normative data and layer thickness distribution acquired for the subject's eye are compared with each other for each of the plurality of regions described above. In addition, a statistical value calculated from the layer thickness distribution of the subject's eye can be compared with the normative data. The statistical value may be, for example, a maximum value, a minimum value, an average value, a mode value, a median value, a range (a difference between the maximum value and the minimum value), a standard deviation, or a variance.

For example, thinning (or loss) of nerve fiber layer may appear in glaucomatous eyes, and normative data defines a threshold value for detecting the thinning of nerve fiber layer. When the axial length of the subject's eye belongs to the standard range, the definition area of the normative data and the area of the layer thickness distribution acquired for the subject's eye substantially agree with each other. Therefore, the comparison between both areas can be preferably performed.

On the other hand, for a subject's eye (E2) whose axial length is longer than the standard, as shown in FIG. 2A, the area A2 of the layer thickness distribution acquired for the subject's eye becomes wider than the definition area A0 of the normative data. Considering that the values of the nerve fiber layer thickness is decreasing toward the periphery of the fundus in general, the comparison result indicating "thinning" is obtained even in the event that the nerve fiber layer of the subject's eye is not actually thinning (false positive) since the area A2 includes a site, located outside the original area A0, whose layer thickness is originally thin.

Conversely, in the subject's eye whose axial length is shorter than the standard, as shown in FIG. 2B, the area A3 of the layer thickness distribution acquired for the subject's eye becomes narrower than the definition area A0 of the normative data. Therefore, the comparison result indicating "not thinning" is obtained even in the event that the nerve fiber layer of the subject's eye is actually thinning (false negative).

In order to prevent such false determination, magnification correction techniques for OCT based on ocular optical system parameters (eyeball optical system parameters) such as eye refractive power, corneal curvature radius or axial length have been proposed. Such techniques are disclosed in, for example, Japanese Unexamined Patent Application Publication No. Hei 10-179517 (No. 1998-179517), Japanese Unexamined Patent Application Publication No. 2006-122160, Japanese Unexamined Patent Application Publication No. 2008-206684, Japanese Unexamined Patent Application Publication No. 2009-000354, Japanese Unexamined Patent Application Publication No. 2016-043155, Japanese Unexamined Patent Application Publication No. Hei 08-206081 (No. 1996-206081), and Japanese Unexamined Patent Application Publication No. 2008-237237. However, such conventional techniques perform the magnification correction using data acquired by an ophthalmic apparatus (an external device) other than an apparatus that acquires OCT data. Therefore, there is a problem that the conventional techniques cannot be applied to screening examinations such as health check and to examinations performed at facilities that do not have the above external device.

DETAILED DESCRIPTION

Figure 1:
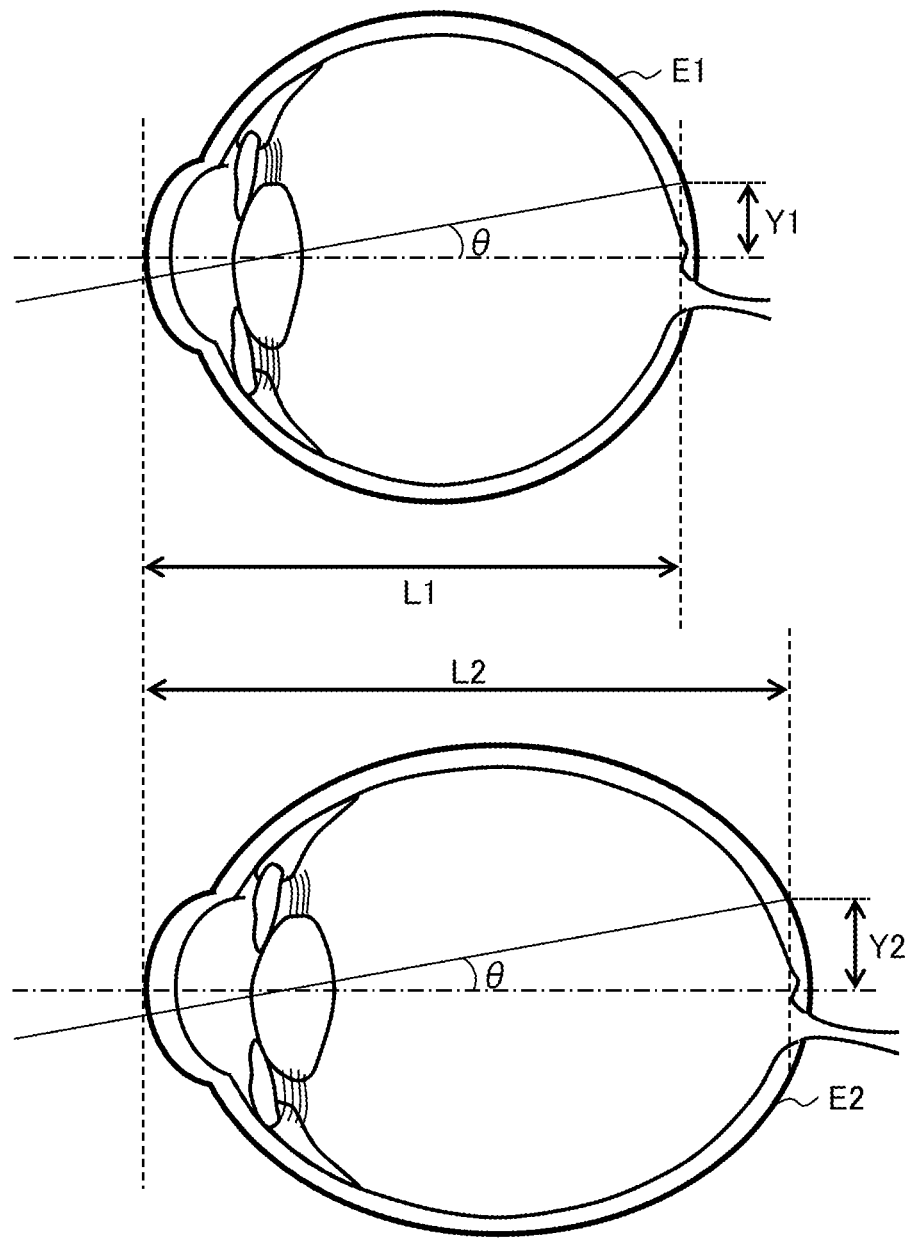
FIG. 1 is a schematic diagram for describing the background.
Figure 2A:
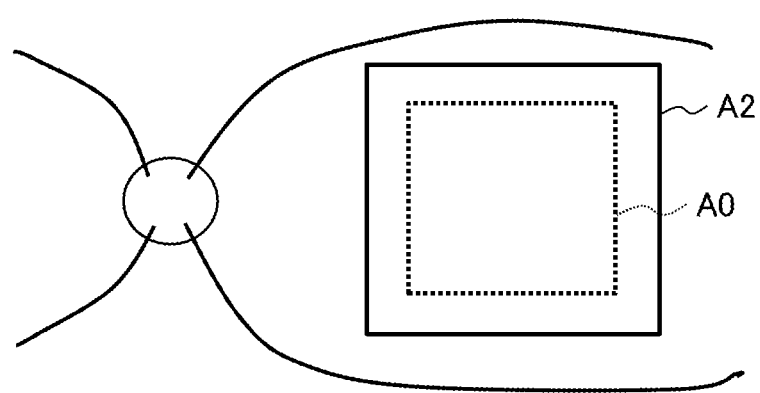
FIG. 2A is a schematic diagram for describing the background.
Figure 2B:
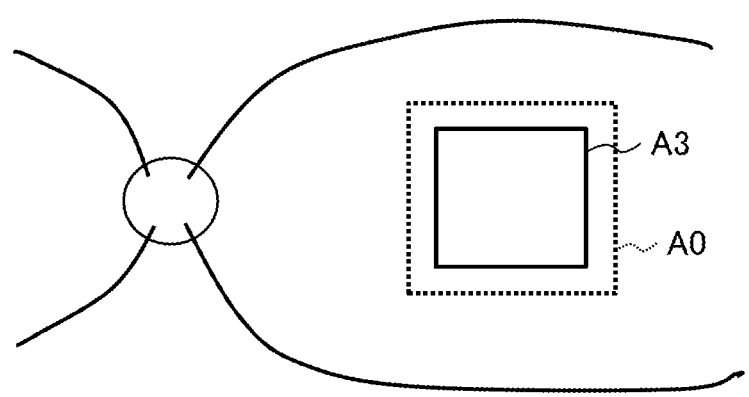
FIG. 2B is a schematic diagram for describing the background.

The first aspect of some embodiments is an ophthalmic apparatus comprising: a data acquisition device that acquires three dimensional data by applying optical coherence tomography to a fundus of a subject's eye; a distribution data generator that generates distribution data of a predetermined measurement value in the fundus based on the three dimensional data; a correction value calculator that calculates a magnification correction value based on a predetermined condition for acquiring the three dimensional data; a magnification corrector that changes at least one of a size of standard distribution data generated in advance for the predetermined measurement value and a size of the distribution data, based on the magnification correction value; and a data comparator that compares the standard distribution data and the distribution data with each other, at least one of whose sizes has been changed by the magnification corrector.

The second aspect of some embodiments is the ophthalmic apparatus of the first aspect, wherein the correction value calculator comprises a first calculator that calculates an estimated value of axial length of the subject's eye based on the predetermined condition, and the correction value calculator calculates the magnification correction value based on at least the estimated value of the axial length.

The third aspect of some embodiments is the ophthalmic apparatus of the second aspect, further comprising an alignment device for performing alignment of the data acquisition device with respect to the subject's eye, wherein the data acquisition device comprises: an interference optical system that splits light from a light source into measurement light and reference light, projects the measurement light onto the fundus, generates interference light by superposing returning light of the measurement light from the subject's eye on the reference light, and detects the interference light; and an optical path length changing device that changes at least one of an optical path length of the measurement light and an optical path length of the reference light, and the first calculator calculates the estimated value of the axial length based on at least a result of the alignment, the optical path length of the measurement light, and the optical path length of the reference light.

The fourth aspect of some embodiments is the ophthalmic apparatus of the third aspect, wherein the alignment device performs the alignment based on a Purkinje image formed by projecting a light beam onto the subject's eye, and the first calculator calculates the estimated value of the axial length based on a relative position between the Purkinje image and the data acquisition device after the alignment, the optical path length of the measurement light and the optical path length of the reference light when the three dimensional data has been acquired, and a standard value of a corneal curvature radius set in advance.

The fifth aspect of some embodiments is the ophthalmic apparatus of the third aspect, wherein the alignment device performs the alignment based on two or more anterior eye segment images acquired by imaging the subject's eye from different directions from each other, and the first calculator calculates the estimated value of the axial length based on a relative position between a pupil of the subject's eye and the data acquisition device after the alignment, the optical path length of the measurement light and the optical path length of the reference light when the three dimensional data has been acquired, a standard value of a corneal thickness set in advance, and a standard value of anterior chamber depth set in advance.

The sixth aspect of some embodiments is the ophthalmic apparatus of any of the first to fifth aspects, wherein the correction value calculator comprises a second calculator that calculates an estimated value of diopter of the subject's eye based on the predetermined condition, and the correction value calculator calculates the magnification correction value based on at least the estimated value of the diopter.

The seventh aspect of some embodiments is the ophthalmic apparatus of the sixth aspect, wherein the data acquisition device comprises an interference optical system that splits light from a light source into measurement light and reference light, projects the measurement light onto the fundus, generates interference light by superposing returning light of the measurement light from the subject's eye on the reference light, and detects the interference light, the ophthalmic apparatus further comprises a focus adjustment device for performing focus adjustment of the interference optical system, and the second calculator calculates the estimated value of the diopter based on a focus state of the interference optical system.

The eighth aspect of some embodiments is the ophthalmic apparatus of the seventh aspect, wherein the focus adjustment device comprises: a focusing lens disposed in an optical path of the measurement light; and a driver that moves the focusing lens along the optical path of the measurement light, and the second calculator calculates the estimated value of the diopter based on at least a position of the focusing lens in the optical path of the measurement light.

The ninth aspect of some embodiments is the ophthalmic apparatus of the seventh aspect, wherein the focus adjustment device detects an indicator image formed by projecting a light beam onto the fundus, and the second calculator calculates the estimated value of the diopter based on the indicator image.

The tenth aspect of some embodiments is an ophthalmic apparatus comprising: a data acquisition device that acquires three dimensional data by applying optical coherence tomography to a fundus of a subject's eye; a distribution data generator that generates distribution data of a predetermined measurement value in the fundus based on the three dimensional data; a data supplementation device that supplements the distribution data based on predetermined information when the distribution data does not comprise data corresponding to part of standard distribution data generated in advance for the predetermined measurement value; and a data comparator that compares the distribution data after supplementation with the standard distribution data.

The eleventh aspect of some embodiments is an ophthalmic apparatus comprising: a reception part that receives three dimensional data acquired by applying optical coherence tomography to a fundus of a subject's eye and a predetermined condition for acquiring the three dimensional data; a distribution data generator that generates distribution data of a predetermined measurement value in the fundus based on the three dimensional data; a correction value calculator that calculates a magnification correction value based on the predetermined condition; a magnification corrector that changes at least one of a size of standard distribution data generated in advance for the predetermined measurement value and a size of the distribution data, based on the magnification correction value; and a data comparator that compares the standard distribution data and the distribution data with each other, at least one of whose sizes has been changed by the magnification corrector.

The twelfth aspect of some embodiments is an ophthalmic apparatus comprising: a reception part that receives distribution data, generated based on three dimensional data acquired by applying optical coherence tomography to a fundus of a subject's eye, of a predetermined measurement value in the fundus and a predetermined condition for acquiring the three dimensional data; a correction value calculator that calculates a magnification correction value based on the predetermined condition; a magnification corrector that changes at least one of a size of standard distribution data generated in advance for the predetermined measurement value and a size of the distribution data, based on the magnification correction value; and a data comparator that compares the standard distribution data and the distribution data with each other, at least one of whose sizes has been changed by the magnification corrector.

The thirteenth aspect of some embodiments is an ophthalmic apparatus comprising: a reception part that receives three dimensional data acquired by applying optical coherence tomography to a fundus of a subject's eye; a distribution data generator that generates distribution data of a predetermined measurement value in the fundus based on the three dimensional data; a data supplementation device that supplements the distribution data based on predetermined information when the distribution data does not comprise data corresponding to part of standard distribution data generated in advance for the predetermined measurement value; and a data comparator that compares the distribution data after supplementation with the standard distribution data.

The fourteenth aspect of some embodiments is an ophthalmic apparatus comprising: a reception part that receives distribution data, generated based on three dimensional data acquired by applying optical coherence tomography to a fundus of a subject's eye, of a predetermined measurement value in the fundus; a data supplementation device that supplements the distribution data based on predetermined information when the distribution data does not comprise data corresponding to part of standard distribution data generated in advance for the predetermined measurement value; and a data comparator that compares the distribution data after supplementation with the standard distribution data.

The fifteenth aspect of some embodiments is a method of controlling the ophthalmic apparatus of any of the first to fourteenth aspects.

The sixteenth aspect of some embodiments is an medical method implemented by the ophthalmic apparatus of any of the first to fourteenth aspects.

Any of the items described in the following disclosure can be combined with each of the first to sixteenth aspects of some embodiments.

Hereinafter, an ophthalmic apparatus and a computer program according to exemplary embodiments will be described in detail with referring to the drawings. The ophthalmic apparatus according to the embodiment has a function of analyzing data acquired by applying OCT to a living eye. The analysis function can perform, for example, normative data comparative analysis. Any known techniques can be incorporated in the embodiments, including any contents of the disclosure of the documents cited in the present specification.

In the exemplary embodiments described below, ophthalmic apparatuses capable of measuring the fundus of a living eye using Fourier domain OCT (particularly swept source OCT) will be described. The type of OCT is not limited to swept source and may be spectral domain OCT or time domain OCT, for example. The ophthalmic apparatuses according to the embodiments are multifunctional apparatuses that are a combination of an OCT apparatus and a fundus camera (retinal camera). However, any kind of fundus photographing apparatus other than a fundus camera may be combined with an OCT apparatus. Examples of such a fundus photographing apparatus include a scanning laser ophthalmoscope (SLO), a slit lamp microscope, and an ophthalmic microscope for surgery.

First Embodiment

<Configuration>

Figure 3:
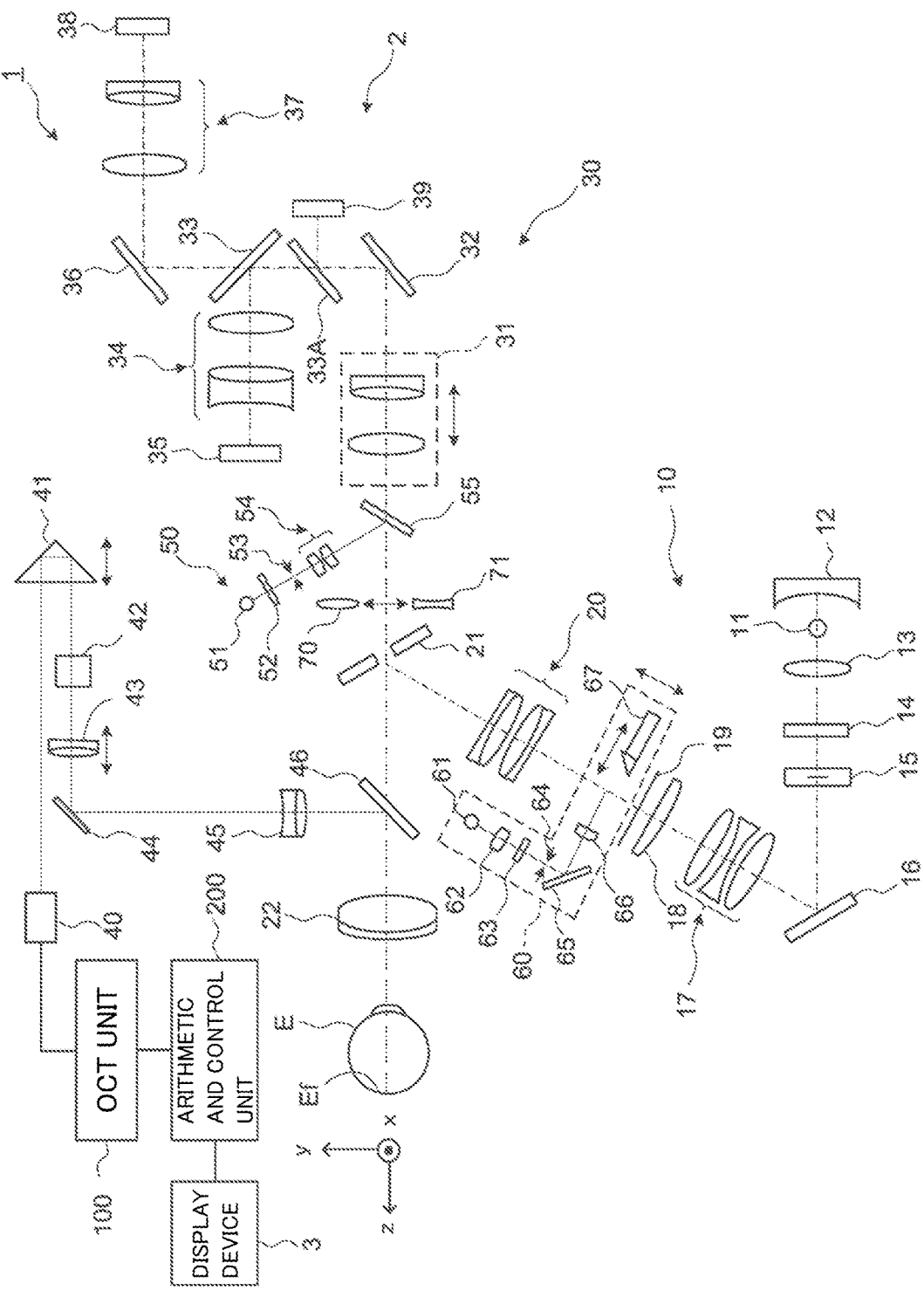
FIG. 3 is a schematic diagram illustrating an example of the configuration of an ophthalmic apparatus according to the embodiment.

As shown in FIG. 3, the ophthalmic apparatus 1 includes the fundus camera unit 2, the OCT unit 100 and the arithmetic and control unit 200. The fundus camera unit 2 is provided with an optical system and a mechanism for acquiring front images of the subject's eye. The OCT unit 100 includes part of an optical system and part of mechanisms for performing OCT. Another part of the optical system and another part of the mechanisms for performing OCT are provided in the fundus camera unit 2. The arithmetic and control unit 200 includes one or more processors that execute various calculations and controls. In addition to these, the ophthalmic apparatus 1 may also include any elements or units such as a member for supporting the face of the subject (e.g., a chin rest, a forehead rest) and a lens unit for switching the sites subjected to OCT imaging (e.g., an attachment for an anterior eye segment OCT).

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the fundus Ef of the subject's eye E. Images of fundus Ef (referred to as fundus images, fundus photographs, or the like) obtained include front images such as observation images and photographed images. An observation image is obtained by capturing a moving image using near-infrared light. A photographed image is a still image obtained by using flash light in the visible range.

The fundus camera unit 2 includes the illumination optical system 10 and the photographing optical system 30. The illumination optical system 10 projects illumination light onto the subject's eye E. The photographing optical system 30 detects the returning light of the illumination light from the subject's eye E. The measurement light incident from the OCT unit 100 is directed to the subject's eye E through the optical path in the fundus camera unit 2, and the returning light thereof is directed to the OCT unit 100 through the same optical path.

The light output from the observation light source 11 of the illumination optical system 10 (called observation illumination light) is reflected by the concave mirror 12, passes through the condenser lens 13, and becomes near-infrared light after passing through the visible cut filter 14. Further, the observation illumination light is once converged near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef thereof). The returning light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Further, the returning light passes through the half mirror 33A, is reflected by the dichroic mirror 33, and forms an image on the light receiving surface of the image sensor 35 by the imaging lens 34. The image sensor 35 detects the returning light at a predetermined frame rate. Note that the focus of the photographing optical system 30 is adjusted to coincide with the fundus Ef or the anterior eye segment.

The light output from the photographing light source 15 (called photographing illumination light) passes through the same route as that of the observation illumination light and is projected onto the fundus Ef. The returning light of the photographing illumination light from the subject's eye E passes through the same route as that of the returning light of the observation illumination light, is guided to the dichroic mirror 33, passes through the dichroic mirror 33, is reflected by the mirror 36, and forms an image on the light receiving surface of the image sensor 38 by the imaging lens 37.

The liquid crystal display (LCD) 39 displays a fixation target (fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the followings: a fixation position for acquiring an image centered on the macula; a fixation position for acquiring an image centered on the optic nerve head; a fixation position for acquiring an image centered on the fundus center that is located between the macula and the optic nerve head; and a fixation position for acquiring an image of a site far away from the macula (periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, capable of changing the fixation position, to the subject's eye E is not limited to display devices such as an LCD. For example, a fixation matrix can be adopted in place of a display device. The fixation matrix includes a plurality of light emitting parts (e.g., light emitting diodes) that are disposed in a matrix-like arrangement (in an matrix array). In this case, the fixation position of the subject's eye E by the fixation target can be changed by lighting one (or more) of the plurality of light emitting parts in a selective manner. As another example, the fixation target that is capable of changing the fixation position can be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The returning light of the alignment light from the subject's eye E (the cornea reflection light, etc.) passes through the same route as that of the returning light of the observation illumination light and is guided to the image sensor 35. Based on the received image (called the alignment indicator image), manual alignment and/or automatic alignment can be performed.

As in a conventional case, the alignment indicator image of the present example includes two bright spot images whose positions change according to the alignment state. When the relative position between the subject's eye E and the optical system changes in the xy direction, the two bright spot images are shifted in the xy direction in an integrated manner. When the relative position between the subject's eye E and the optical system changes in the z direction, the relative position (distance) between the two bright spot images changes. When the distance between the subject's eye E and the optical system in the z direction matches a predetermined working distance, the two bright spot images overlap with each other. When the position of the subject's eye E matches the position of the optical system in the xy direction, the two bright spot images are presented within or near a given alignment target. When the distance between the subject's eye E and the optical system in the z direction matches the working distance, and the position of the subject's eye E matches the position of the optical system in the xy direction, the two bright spot images overlap with each other and are presented within the alignment target.

In the automatic alignment, the data processor 230 detects the positions of the two bright spot images, and the main controller 211 controls the movement mechanism 150 (described later) on the basis of the positional relationship between the two bright spot images and the alignment target. In the manual alignment, the main controller 211 displays the two bright spot images together with the observation image of the subject's eye E on the display 241, and the user operates the movement mechanism 150 using the operation device 242 while referring to the two bright spot images displayed.

The focus optical system 60 generates a split indicator used for the focus adjustment with respect to subject's eye E. In conjunction with the movement of the photography focusing lens 31 along the optical path of the photographing optical system 30 (referred to as the photographing optical path), the focus optical system 60 is moved along the optical path of the illumination optical system 10 (called the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The returning light of the focus light from the subject's eye E (the fundus reflection light, etc.) passes through the same route as the returning light of the alignment light and is guided to the image sensor 35. Based on the image (called the split indicator image), manual focusing and/or automatic focusing can be performed.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT (measurement arm). The dichroic mirror 46 reflects the light of wavelength bands used for OCT and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrow in FIG. 3, whereby the length of the measurement arm is changed. The change in the length of the measurement arm can be utilized for correcting the optical path length according to the axial length, and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is moved along the measurement arm in order to perform the focus adjustment of the measurement arm. The movement of the photography focusing lens 31, the movement of the focus optical system 60, and the movement of the OCT focusing lens 43 can be controlled in an interlocking manner.

The optical scanner 44 is substantially placed at a position optically conjugate with the pupil of the subject's eye E. The optical scanner 44 deflects the measurement light LS guided through the measurement arm. The optical scanner 44 is, for example, a galvano scanner capable of two dimensional scanning.

<OCT Unit 100>

Figure 4:
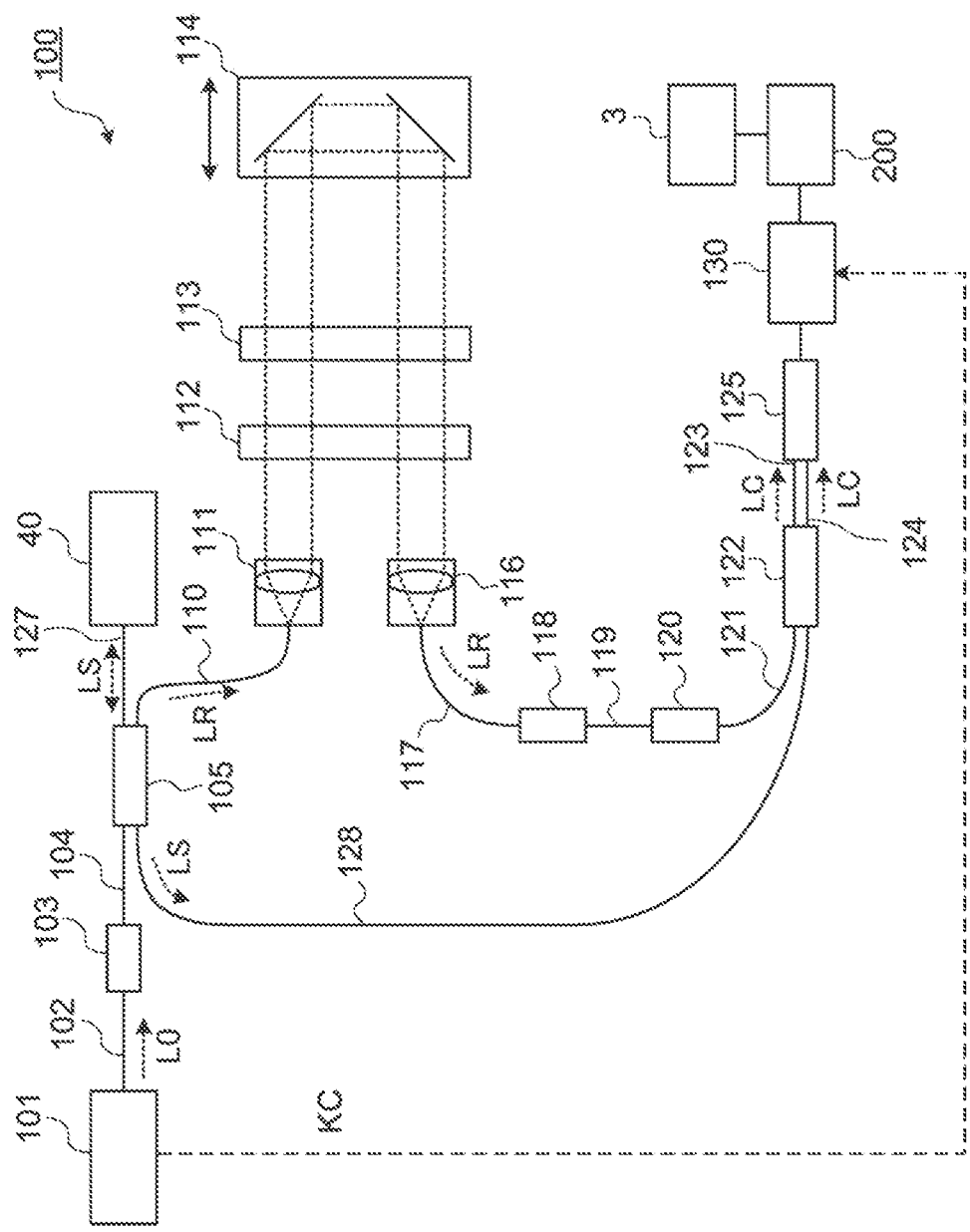
FIG. 4 is a schematic diagram illustrating an example of the configuration of the ophthalmic apparatus according to the embodiment.

As illustrated in FIG. 4, the OCT unit 100 is provided with the optical system for performing swept source OCT. The optical system includes an interference optical system. The interference optical system is configured to split the light emitted from the light source of wavelength tunable type (also called wavelength swept type) into measurement light and reference light, superpose the returning light of the measurement light from the subject's eye E and the reference light having traveled through the reference optical path to generate interference light, and detect the interference light. The detection result (i.e., detection signal) obtained by the interference optical system is a signal representing a spectrum of the interference light. The detection signal is sent to the arithmetic and control unit 200.

The light source unit 101 includes, for example, a near infrared tunable laser configured to change the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 11, is converted into a parallel light beam, travels through the optical path length correction member 112 and the dispersion compensation member 113, and is guided to the retroreflector 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the length of the reference arm can be utilized, for example, for the correction of the optical path length according to the axial length, and for the regulation of the interference condition.

The reference light LR that has passed through the retroreflector 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The returning light of the measurement light LS from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 and the reference light LR incident through the optical fiber 121 with each other, to generate interference light. The fiber coupler 122 splits the generated interference light at a predetermined splitting ratio (e.g., 1 to 1) to generate a pair of interference light LC. The pair of the interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, optically delays one of the two pieces of split light, combines the two pieces of split light, detects the combined light obtained, and generates the clock KC based on the result of the detection of the combined light. The data acquisition system 130 performs the sampling of the detection signal input from the detector 125 based on the clock KC. The data acquisition system 130 sends the result of the sampling of the detection signal from the detector 125 to the arithmetic and control unit 200.

The present example is provided with both an element for changing the length of the measurement arm (e.g., the retroreflector 41) and an element for changing the length of the reference arm (e.g., the retroreflector 114 or a reference mirror). However, only one of these elements may be provided in other embodiments. An element for changing the difference between the length of the measurement arm and the length of the reference arm (i.e., an element for changing the optical path length difference) are not limited to the aforesaid elements, and may be any type of element (e.g., any optical member, any mechanism).

<Control System>

Figure 5:
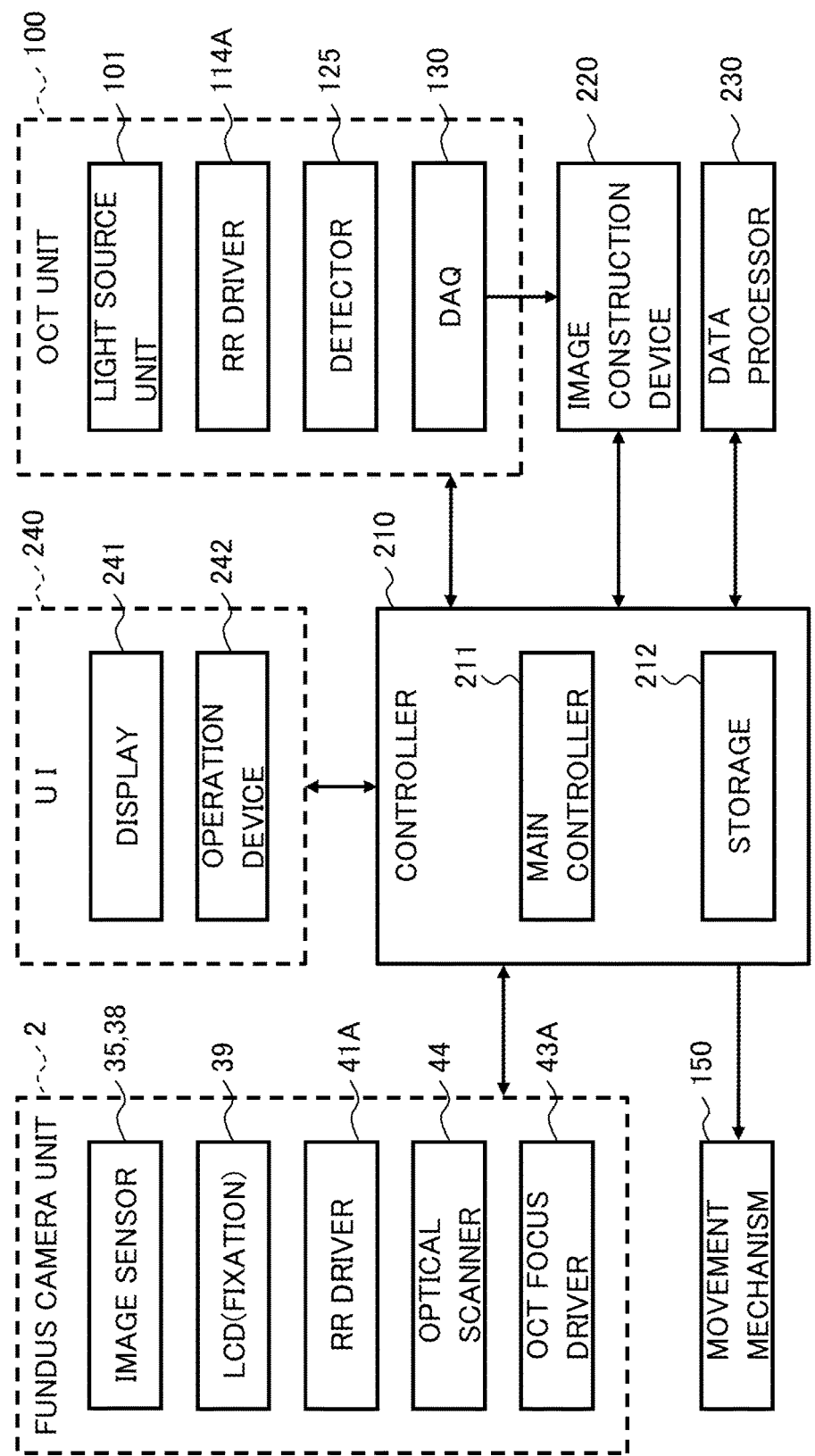
FIG. 5 is a schematic diagram illustrating an example of the configuration of the ophthalmic apparatus according to the embodiment.
Figure 6A:
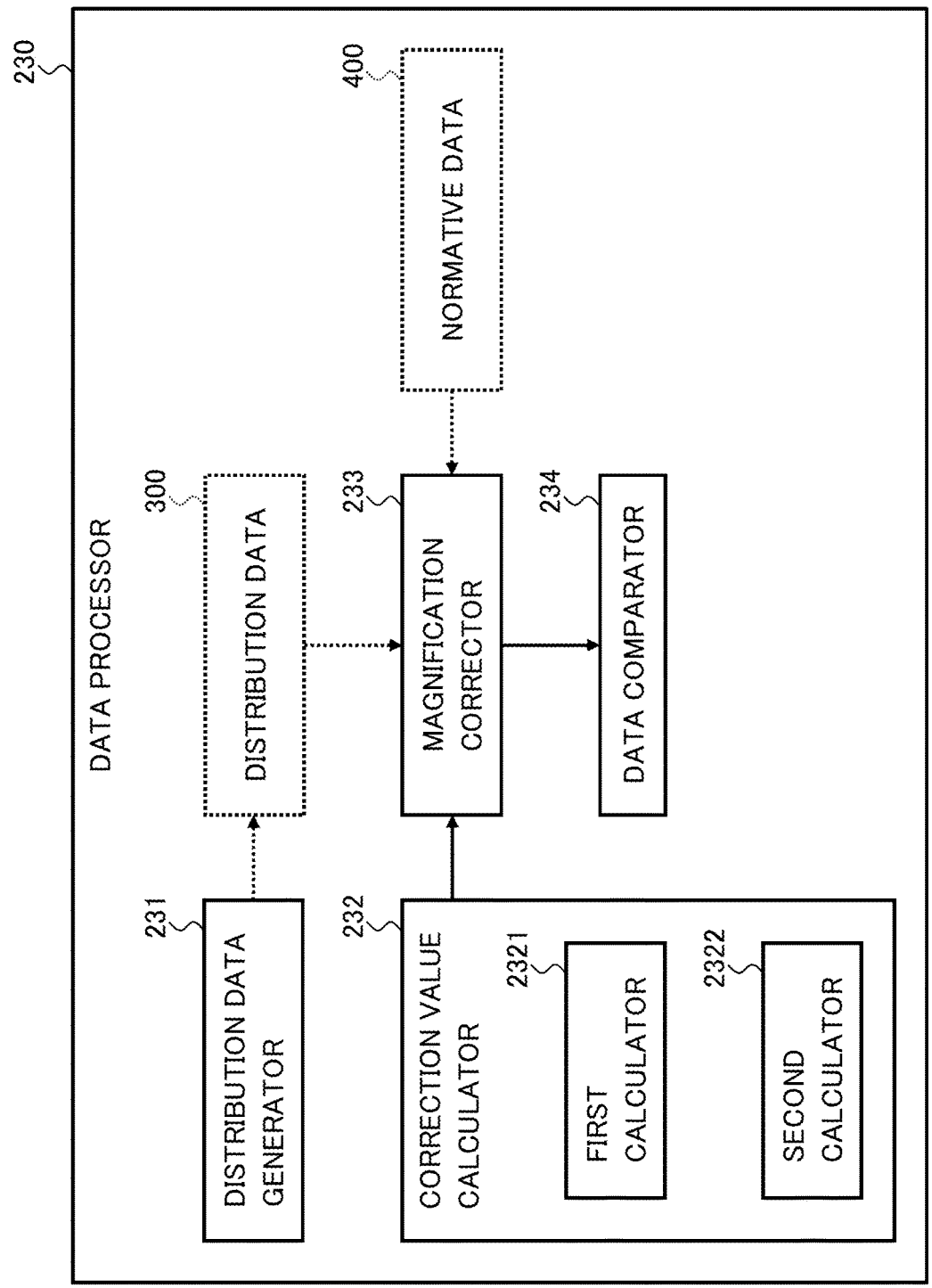
FIG. 6A is a schematic diagram illustrating an example of the configuration of the ophthalmic apparatus according to the embodiment.
Figure 6B:
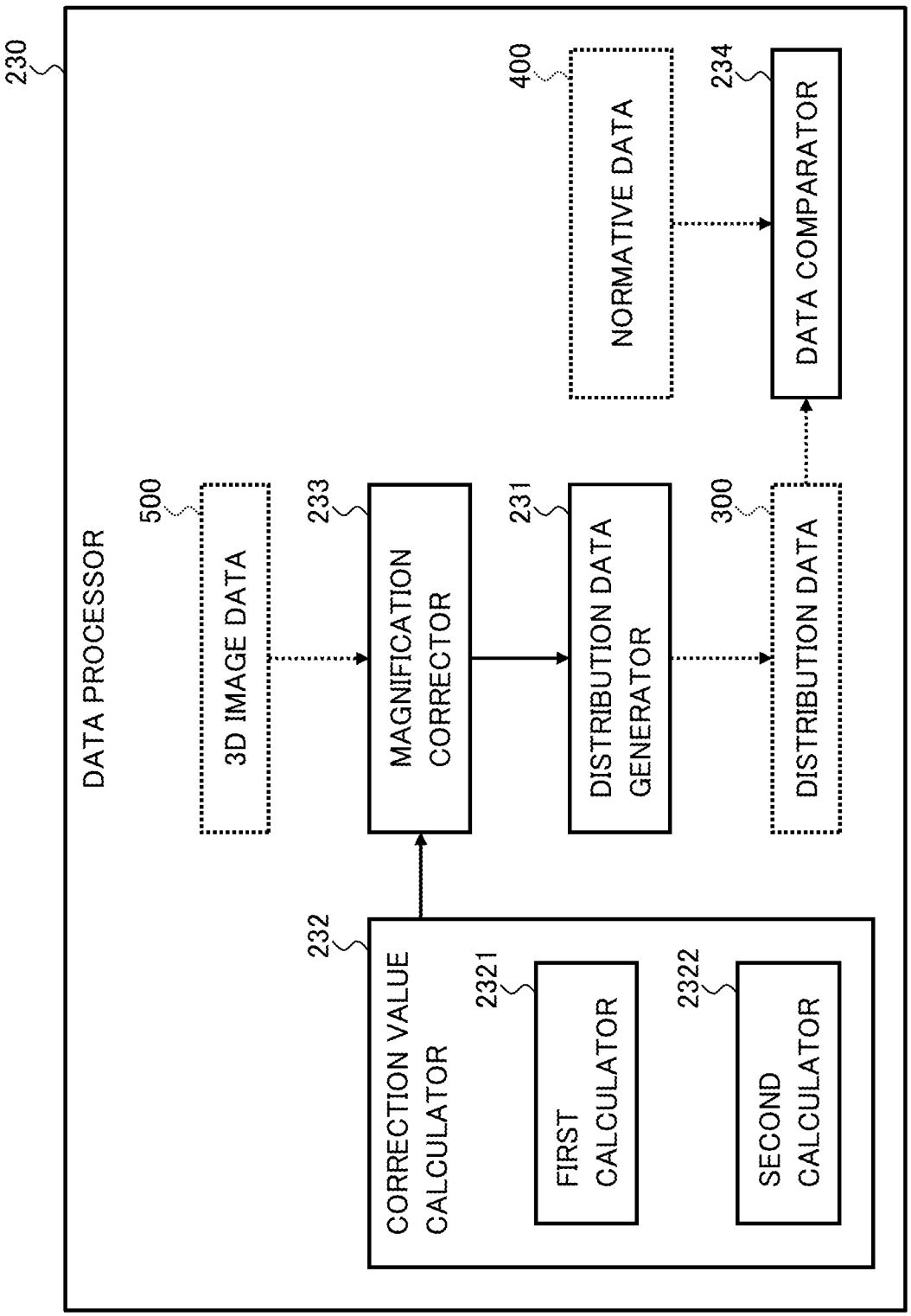
FIG. 6B is a schematic diagram illustrating an example of the configuration of the ophthalmic apparatus according to the embodiment.

FIG. 5, FIG. 6A and FIG. 6B show an example of the configuration of the control system of the ophthalmic apparatus 1. The controller 210, the image construction device 220 and the data processor 230 are provided, for example, in the arithmetic and control unit 200.

<Controller 210>

The controller 210 performs various kinds of controls. The controller 210 includes the main controller 211 and the storage 212.

<Main Controller 211>

The main controller 211 includes a processor and controls each element of the ophthalmic apparatus 1 (including the elements shown in FIG. 3 to FIG. 6B).

The photography focusing lens 31 disposed in the photographing optical path and the focus optical system 60 disposed in the illumination optical path are moved by a photographing focus driver (not shown) under the control of the main controller 211. The retroreflector 41 disposed in the measurement arm is moved by the retroreflector driver (RR driver) 41A under the control of the main controller 211. The OCT focusing lens 43 disposed in the measurement arm is moved by the OCT focus driver 43A under the control of the main controller 211. The optical scanner 44 disposed in the measurement arm operates under the control of the main controller 211. The retroreflector 114 disposed in the reference arm is moved by the retroreflector driver (RR driver) 114A under the control of the main controller 211. Each of the aforesaid drivers includes an actuator such as a pulse motor which operates under the control of the main controller 211.

The movement mechanism 150 moves, for example, at least the fundus camera unit 2 in a three dimensional manner. In a typical example, the movement mechanism 150 includes the followings: an x stage movable in the ±x direction (i.e., left and right direction); an x movement mechanism that moves the x stage; a y stage movable in the ±y direction (i.e., up and down direction); a y movement mechanism that moves the y stage; a z stage movable in the ±z direction (i.e., depth direction); and a z movement mechanism that moves the z stage. Each of the aforesaid movement mechanisms includes an actuator such as a pulse motor which operates under the control of the main controller 211.

<Storage 212>

The storage 212 stores various kinds of data. Examples of the data stored in the storage 212 include OCT images, fundus images, and subject's eye information. The subject's eye information includes subject information such as the patient ID and the patient's name, identification information for the left eye and the right eye, and electronic medical record information.

In the present embodiment, standard distribution data generated in advance is stored in the storage 212. The standard distribution data is data representing a distribution of a predetermined measurement value that can be referred to in diagnostic imaging using OCT and image analysis. The predetermined measurement value is typically the thickness of a predetermined layer tissue of retina. The layer tissue may be nerve fiber layer, ganglion cell layer, or another tissue. However, the predetermined measurement value is not limited to the layer thickness.

The standard distribution data includes, for example, values obtained by statistically processing a sample of the predetermined measurement values acquired from a large number of normal eyes. Typically, the standard distribution data represents a distribution of normal ranges calculated from a sample of layer thickness values obtained by applying OCT to the funduses of a large number of normal eyes. Each of the normal ranges can be set to include, for example, an average value derived from the sample. The standard distribution data generated based on the normal eyes in this way is called normative data. Note that the standard distribution data may be generated based on a plurality of eyes suffering from a specific disease.

The standard distribution data is, for example, a distribution in a predetermined area including a predetermined site of eye fundus. In a typical example, the standard distribution data is generated by assigning a normal range of the layer thickness value of the normal eyes, to each of a plurality of sections that are formed by dividing, in a grid-like manner, a rectangular region of 6 mm×6 mm in which fovea centralis is placed at the center. A standard distribution data created in this way can be used as the normative data 400 shown in FIG. 6A and FIG. 6B. The normative data 400 may be known data.

The standard distribution data can be prepared for each of two or more diseases and selectively used. The standard distribution data can be prepared for each of two or more attributes of subjects (e.g., age groups) and selectively used. The standard distribution data can be prepared for each of two or more attributes of subject's eyes (e.g., highly myopic eyes and others) and selectively used.

<Image Construction Device 220>

The image construction device 220 constructs OCT image data of the fundus Ef based on the signal (sampling data) input from the data acquisition system 130. The OCT image data is, for example, B-scan image data (i.e., two dimensional cross sectional image data). The processing for constructing OCT image data includes noise elimination (or noise reduction), filtering, fast Fourier transform (FFT), and other processes as in a conventional Fourier domain OCT. In the event that another type of OCT apparatus is used, the image construction device 220 performs known processing according to the OCT type employed. The image construction device 220 includes a processor. In this specification, "image data" and an "image" formed based on the "image data" may not be distinguished unless otherwise mentioned.

<Data Processor 230>

The data processor 230 applies various kinds of image processing and/or analysis to the image constructed by the image construction device 220. For example, the data processor 230 is configured to be capable of executing various kinds of correction processing such as brightness correction and dispersion correction of an image. Further, the data processor 230 can perform various kinds of image processing and/or various kinds of analysis on an image (e.g., a fundus image, an anterior eye segment image) obtained by the fundus camera unit 2.

The data processor 230 can construct three dimensional image data of fundus Ef. Three dimensional image data means image data in which the positions of pixels are defined using a three dimensional coordinate system. Stack data and volume data are examples of three dimensional image data.

Stack data is image data constructed by arranging a plurality of cross sectional images obtained along a plurality of scan lines in an three dimensional fashion, based on the positional relationship of the scan lines. More specifically, stack data is image data constructed by representing a plurality of cross sectional images, which are originally defined using individual two dimensional coordinate systems, using a common three dimensional coordinate system. In other words, stack data is image data constructed by embedding a plurality of cross sectional images in a single three dimensional space.

Volume data is image data whose picture elements are voxels that are arranged in a three dimensional manner. Volume data is also referred to as voxel data. Volume data is constructed by applying known interpolation, voxelization, or the like, to stack data.

The data processor 230 can construct an image to be displayed, by applying rendering to three dimensional image data. Examples of applicable rendering methods include volume rendering, surface rendering, maximum intensity projection (MIP), minimum intensity projection (MiniP), and multi planar reconstruction (MPR).

Each of FIG. 6A and FIG. 6B shows an example of the configuration of the data processor 230. The data processor 230 includes the distribution data generator 231, the correction value calculator 232, the magnification corrector 233, and the data comparator 234. Hereinafter, the example shown in FIG. 6A will be mainly described.

<Distribution Data Generator 231>

In the present embodiment, a three dimensional scan (also called a volume scan) is applied to the fundus Ef. A three dimensional scan is an OCT scan for a three dimensional region of the fundus Ef. The mode of a three dimensional scan may be optional. For example, a raster scan is used as a three dimensional scan. The ophthalmic apparatus 1 (i.e., the image construction device 220 and the data processor 230) processes data acquired through a three dimensional scan (i.e., processes three dimensional data) to construct three dimensional image data.

The distribution data generator 231 generates distribution data of a predetermined measurement value in the fundus Ef based on the three dimensional image data constructed. As described above, the predetermined measurement value is referred to in diagnostic imaging using OCT and image analysis, and is of the same kind as the measurement value represented by the standard distribution data. The present example will describe a case where the predetermined measurement value is the thickness of a predetermined layer tissue (e.g., nerve fiber layer, ganglion cell layer) of retina and the standard distribution data is the normative data 400 will be described. However, the predetermined measurement value is not limited to the layer thickness. The distribution data generated by the distribution data generator 231 is used as the distribution data 300 shown in FIG. 6A and FIG. 6B.

In the present example, the distribution data generator 231 generates layer thickness distribution data representing a distribution of the thickness of the predetermined layer tissue in the retina of the fundus Ef. The contents (or details) of the processing executed by the distribution data generator 231 to generate the layer thickness distribution data is optional.

In one example the distribution data generator 231 includes the following processing as with a conventional manner: a process of dividing three dimensional image data into a plurality of pieces of partial image data by applying segmentation to the three dimensional image data; a process of specifying (selecting) the partial image data corresponding to the predetermined layer tissue from among the plurality of pieces of partial image data; and a process of determining (calculating) the thickness of the predetermined layer tissue at each of a plurality of positions, based on the partial image data specified (selected).

<Correction Value Calculator 232>

The correction value calculator 232 calculates a magnification correction value based on one or more predetermined conditions for acquiring three dimensional data of the fundus Ef using a three dimensional OCT scan.

The correction value calculator 232 includes the first calculator 2321 and the second calculator 2322. The first calculator 2321 is configured to calculate an estimated value of the axial length of the subject's eye E. The second calculator 2322 is configured to calculate an estimated value of the diopter (refractive power) of the subject's eye E. The correction value calculator 232 is configured to determine a magnification correction value based on at least one of the estimated value of the axial length and the estimated value of the diopter. Note that a value used for calculating a magnification correction value is not limited to the aforesaid values, and may be any characteristic value relating to the subject's eye E.

In the present example, the predetermined conditions include a condition related to alignment, a condition related to focus (focusing, focal position), and a condition related to the OCT optical path length. The condition related to alignment and the condition related to the OCT optical path length are used for the calculation of the estimated value of the axial length carried out by the first calculator 2321. The condition related to focus is used for the calculation of the estimated value of the diopter carried out by the second calculator 2322.

<First Calculator 2321>

The calculation of the estimated value of the axial length carried out by the first calculator 2321 will be described. As an example, the method described in Japanese Unexamined Patent Application Publication No. 2008-237237 can be applied. More specifically, given that the optical path length of the reference arm is denoted by $OPL_R$, the optical path length of the measurement arm is denoted by $OPL_S$, the working distance is denoted by WD, and the intraocular distance between the position where the measurement light LS is incident on the subject's eye E and the position where the measurement light LS is reflected at the fundus Ef is denoted by D, there is the following relationship between these parameters: $OPL_R = OPL_S + WD + D$. From this, the intraocular distance D (that is, the estimated value of the axial length D) can be expressed as follows: $D = OPL_R - OPL_S - WD$.

When the alignment of the optical system of the ophthalmic apparatus 1 with respect to the subject's eye E has been performed in a proper manner, the optical system (the objective lens 22) is located at a position away from the subject's eye E by the preset working distance WD in the −z direction. As such, in the present example, the working distance WD is a preset constant, and on condition that the alignment has been completed (furthermore, the subsequent tracking has been performed in an appropriate manner), it is assumed that the distance between the optical system and the subject's eye E is equal to the working distance WD, and the constant WD is applied. In the present example, the working distance WD corresponds to the condition related to alignment.

The condition related to alignment is not limited to such a default value of working distance. For example, when a configuration that is capable of determining the distance (the distance in the z direction) between the subject's eye E and the optical system is adopted, as in the case of performing alignment using two or more cameras that are capable of imaging the subject's eye E from mutually different directions, the value of the distance thus determined can be used as the condition related to alignment instead of the working distance WD.

In general, prior to applying an OCT scan to the fundus Ef, the optical path length adjustment of the interference optical system is performed so that an image of the fundus Ef is displayed at a predetermined position in the frame of an OCT image. More specifically, at least one of the optical path length of the measurement arm and the optical path length of the reference arm is adjusted. The change in the optical path length of the measurement arm can be performed by the retroreflector 41 and the retroreflector driver 41A under the control of the main controller 211, for example. The change in the optical path length of the reference arm can be performed by the retroreflector 114 and the retroreflector driver 114A under the control of the main controller 211.

The position of the retroreflector 41 or the operation state of the actuator of the retroreflector driver 41A is detected using a position detector not shown (e.g., a potentiometer, an encoder, etc.), for example. Alternatively, the position of the retroreflector 41 or the operation state of the actuator of the retroreflector driver 41A may be detected based on the control content (control history) of the main controller 211 for the retroreflector driver 41A.

Positions of the retroreflector 41 or operation states of the actuator of the retroreflector driver 41A can be associated with values of the optical path length of the measurement arm in advance. This association is made, for example, based on the design data of the measurement arm. The association information (e.g., table information, graph information, etc.) representing the association is prepared in advance and stored in the storage 212, for example. The first calculator 2321 receives a detection result of the position of the retroreflector 41 (or a detection result of the operation state of the actuator of the retroreflector driver 41A), and determines the value of the optical path length corresponding to the received detection result with referring to the association information. The value of the optical path length determined is used as the optical path length of the measurement arm $OPL_S$.

The optical path length of the reference arm $OPL_R$ can be determined in that same manner. The optical path length of the reference arm $OPL_R$ and the optical path length of the measurement arm $OPL_S$ correspond to the condition related to the OCT optical path length.

When only one of the optical path length of the measurement arm and the optical path length of the reference arm can be varied, the optical path length of one arm whose optical path length can be changed is calculated, for example, in the manner described above. In addition, a preset value (design data) is applied as the optical path length of the other arm whose optical path length is fixed.

The first calculator 2321 can calculate the estimated value of the axial length D by substituting the optical path length of the reference arm $OPL_R$, the optical path length of the measurement arm $OPL_S$, and the working distance WD into the above arithmetic formula "$D = OPL_R - OPL_S - WD$".

<Second Calculator 2322>

The calculation of the estimated value of the diopter carried out by the second calculator 2322 will be described. In general, before applying an OCT scan to the fundus Ef, the OCT focusing lens 43 disposed in the measurement arm is moved by the OCT focus driver 43A under the control of the main controller 211 according to the diopter (refractive power) of the subject's eye E. This processing is carried out, for example, based on the result of the autofocusing of the fundus camera unit 2 using the split indicator (that is, the automatic movement of the photography focusing lens 31 and the focus optical system 60). For example, the autofocusing according to the present embodiment is performed by interlocking controls of the movement of the photography focusing lens 31, the movement of the focusing optical system 60, and the movement of the OCT focusing lens 43, as in a conventional case.

The position of the OCT focusing lens 43 or the operation state of the OCT focus driver 43A (or, the position of the photography focusing lens 31 or the operation state of the photographing focus driver (not shown)) is detected using, for example, a position detector not shown (e.g., a potentiometer, an encoder, etc.). Alternatively, the position of the OCT focusing lens 43 or the operation state of the OCT focus driver 43A (or, the position of the photography focusing lens 31 or the operation state of the photographing focus driver (not shown)) can be detected based on the control content (control history) of the main controller 211 for the OCT focus driver 43A (or for the photographing focus driver). The photography focusing lens 31 and the OCT focusing lens 43 may operate independently of each other. In this case, the movement amount of the OCT focusing lens 43 can be determined on the basis of an evaluation value (e.g., contrast) of an image obtained by a preliminary scan.

Further, positions of the OCT focusing lens 43 or operation states of the actuator of the OCT focus driver 43A (or, positions of the photography focusing lens 31 or operation states of the actuator of the photographing focus driver) can be associated in advance with values of the diopter of eyes. This association is made, for example, based on the design data of the optical system (the measurement arm or the imaging optical system 30). The association information (e.g., table information, graph information, etc.) representing the association is prepared in advance and stored in the storage 212, for example. The second calculator 2322 receives a detection result of the position of the OCT focusing lens 43 (or, a detection result of the operation state of the actuator of the OCT focus driver 43A, a detection result of the position of the photography focusing lens 31, or a detection result of the operation state of the actuator of the photographing focus driver), and determines the value of the diopter corresponding to the received detection result with referring to the association information. The value of the diopter determined is used as an estimated value of the diopter of the subject's eye E.

In this manner, the correction value calculator 232 can determine the estimated value of the axial length and the estimated value of the diopter, from predetermined conditions for acquiring three dimensional data of the fundus Ef with a three dimensional OCT scan. It should be noted that the correction value calculator 232 may be configured to calculate only one of the estimated value of the axial length and the estimated value of the diopter. Further, the estimated value calculable by the correction value calculator 232 is not limited to the estimated value of the axial length and the estimated value of the diopter, but may be an estimated value of any characteristic of the subject's eye E that can be used for calculation of the magnification correction value.

Further, the correction value calculator 232 can calculate the magnification correction value based on one or more estimated values calculated from the predetermined conditions for acquiring three dimensional data. This processing is executed by using the magnification calculation method described in, for example Japanese Unexamined Patent Application Publication No. 2008-206684 or Japanese Unexamined Patent Application Publication No. 2016-043155.

The magnification correction value is calculated as a value defined on the basis of a predetermined reference value. The reference value may be, for example, a value according to the size of the normative data 400 (i.e., 6 mm×6 mm). In this case, a three dimensional scan applied to the fundus Ef is performed with the target of an area of [size in the x direction is 6 mm]×[size in the y direction is 6 mm]. As described above, even if a scan is performed assuming such a target area, the actually scanned area may be larger or smaller than the target area in some cases due to the influence of the axial length and the diopter of the subject's eye E.

The magnification correction value calculated by the correction value calculator 232 corresponds to the ratio of the actual scan area to the target area that has been calculated in consideration of the estimated value of the axial length and the estimated value of the diopter of the subject's eye E. In other words, the magnification correction value is a correction coefficient for equalizing the size of the actual scan area with the size of the target area, and is a correction coefficient for equalizing the size of the target area with the size of the actual scan area.

In the calculation of the magnification correction value, an eye characteristic value different from the one or more estimated values described above can be used. The corneal curvature radius and the intraocular lens power are examples of the eye characteristic value different from the aforesaid estimated values. The eye characteristic value may be, for example, a value acquired by the ophthalmic apparatus 1, a standard value from a model eye etc., or other default values. As an example, when an OCT scan has been applied to the anterior eye segment of the subject's eye E by the ophthalmic apparatus 1, the corneal curvature radius can be determined from the data obtained by the anterior eye segment OCT scan. As another example, the value of the corneal curvature radius in the Gullstrand eye model can be used. As still another example, the power of the intraocular lens implanted in the subject's eye E can be acquired from an electronic medical record or another source.

<Magnification Corrector 233>

The magnification corrector 233 changes at least one of the size of the distribution data 300 generated by the distribution data generator 231 and the size of the normative data 400, based on the magnification correction value calculated by the correction value calculator 232. In other words, the magnification corrector 233 changes the relative size between the normative data 400 and the distribution data 300, based on the magnification correction value calculated by the correction value calculator 232.

As described above, the magnification correction value is a first correction coefficient for equalizing the size of the scan area (area in the xy plane) of the three dimensional scan performed to generate the distribution data 300, with the size of the target area which is the size of the normative data 400. Further, the magnification correction value is a second correction coefficient for equalizing the size of the target area which is the size of the normative data 400, with the size of the scan area of the three dimensional scan performed to generate the distribution data 300. Typically, the first correction coefficient and the second correction coefficient have a reciprocal relationship.

In one example, the magnification corrector 233 can equalize the size of the distribution data 300 with the size of the normative data 400, by multiplying the size of the distribution data 300 by the magnification correction value (the first correction coefficient). In another example, the magnification corrector 233 can equalize the size of the normative data 400 with the size of the distribution data 300, by multiplying the size of the normative data 400 by the magnification correction value (the second correction coefficient). In yet another example, the magnification corrector 233 can equalize the size of the distribution data 300 and the size of the normative data 400 with each other, by multiplying the distribution data 300 by a first correction coefficient and multiplying the normative data 400 by a second correction coefficient, wherein the first and second correction coefficients are different from each other.

<Data Comparator 234>

The data comparator 234 compares the normative data 400 and the distribution data 300 with each other, at least one of whose sizes has been changed by the magnification corrector 233.

For example, when only the size of the normative data 400 has been changed by the magnification corrector 233, the magnification corrector 233 compares the normative data 400 whose size has been changed and the distribution data 300 with each other. Further, when only the size of the distribution data 300 has been changed by the magnification corrector 233, the data comparator 234 compares the distribution data 300 whose size has been changed and the normative data 400 with each other. When both the size of the normative data 400 and the size of the distribution data 300 have been changed by the magnification corrector 233, the data comparator 234 compares the normative data 400 whose size has been changed and the distribution data 300 whose size has been changed with each other. In either case, the data comparator 234 compares the normative data 400 and the distribution data 300 with each other, both of which have substantially the same size.

The comparison process executed by the data comparator 234 can be executed in the same manner as conventional normative data comparative analysis. As a typical example, the normative data 400 is standard distribution data defined for a rectangular region of a predetermined size (e.g., 6 mm×6 mm) in which the fovea centralis is placed at the center. A normal range of the layer thickness of normal eyes is assigned to each of the plurality of sections formed by dividing the rectangular region in a grid-like manner. Here, a plurality of normal ranges may be provided stepwise. In another example, one or more degrees of abnormality may be set in accordance with deviation amounts from a normal range.

On the other hand, the distribution data 300 is, for example, measurement data in which, to each of a plurality of positions in the rectangular region of the fundus Ef to which the raster scan has been applied, the layer thickness value (the measurement value) obtained for the concerned position is assigned. Here, the plurality of positions is typically, the positions of a plurality of A-scans included in the raster scan.

The size of the normative data 400 and the size of the distribution data 300 are substantially matched by the magnification corrector 233. The data comparator 234 performs registration (position matching) between the normative data 400 and the distribution data 300.

Furthermore, the data comparator 234 divides the distribution data 300 into a plurality of sections corresponding to the plurality of sections of the normative data 400.

Next, for each of the plurality of sections of the distribution data 300, the data comparator 234 calculates a statistical value from a plurality of layer thickness values included in the concerned section of the distribution data 300. The statistical value is, for example, any of an average value, a maximum value, a minimum value, a mode value, a median value, and a range (the difference between the maximum value and the minimum value). Typically, the statistical value is the average value.

Subsequently, for each of the plurality of sections of the distribution data 300, the data comparator 234 compares the average value for the concerned section of the distribution data 300, with the normal range (or the abnormal range) assigned to the section of the normative data 400 corresponding to the concerned section of the distribution data 300.

When the average value belongs to the normal range, the layer thickness value in the concerned section of the distribution data 300 is determined to be normal.

On the other hand, when the average value does not belong to the normal range, the layer thickness value in the concerned section of the distribution data 300 is determined to be abnormal. In addition to this, the degree of abnormality of the layer thickness value in the concerned section of the distribution data 300 may be determined by comparing the average value with the preset degrees of abnormality. In other words, it is possible to determine to which of the two or more abnormal ranges the average value belongs.

Further, the data comparator 234 can calculate a statistical value based on two or more average values in two or more sections among the plurality of sections of the distribution data 300. The statistical value may be, for example, a maximum value, a minimum value, an average value, a mode value, a median value, a range, a standard deviation, a variance, or a value of another type. Then, the data comparator 234 can determine the normality and/or abnormality of the layer thickness over the two or more sections in the distribution data 300 by comparing the statistical values on the two or more sections in the distribution data 300 with the same kind of statistical values on two or more corresponding sections in the normative data 400.

The determination result obtained by the data comparator 234 is displayed, for example, as a comparison map. The comparison map shows the normality, the abnormality, the degree of abnormality, and the like of the layer thickness values in the distribution data 300 in a color-coded manner.

When changing the size of the distribution data 300, the size of the data from which the distribution data 300 is generated may be changed in order to change the size of the distribution data 300. FIG. 6B shows an example of the configuration of the data processor 230 applicable in such a case. In the example shown in FIG. 6B, the magnification corrector 233 changes the size of the three dimensional image data 500 constructed by the data processor 230. The distribution data generator 231 constructs the distribution data 300 based on the three dimensional image data 500 whose size has been changed. The data comparator 234 compares the distribution data 300 based on the three dimensional image data 500 whose size has been changed, with the normative data 400.

In another example, the ophthalmic apparatus 1 may be configured to change the sizes of the data from which the three dimensional image data is constructed. For example, the size of the three dimensional data acquired by the three dimensional scan can be changed. Alternatively, it is possible to change the sizes of a plurality of cross sectional images constructed from the three dimensional data (e.g., a plurality of B-scan images when the raster scan is performed) and the relative positional relationship (i.e., arrangement intervals) between the plurality of cross sectional images.

As described above, also in the case of changing the size of any kind of data from which the distribution data 300 is generated, the size of the distribution data 300 is changed as a result. Therefore, the change in the size (the magnification correction) of the distribution data 300 includes not only the magnification correction of the distribution data 300 itself but also the magnification correction of any kind of data from which the distribution data 300 is generated.

<Operation>

An example of the operation of the ophthalmic apparatus 1 will be described. Any preliminary process similar to conventional methods such as the input of a patient ID, the presentation of a fixation target, and the adjustment of the fixation position may be performed at any stage (at any timing).

(S1: Alignment)

First, the ophthalmic apparatus 1 performs alignment of the optical system with respect to the subject's eye E. In the present example, automatic alignment using the alignment indicator is executed. Here, the focus adjustment of the interference optical system (the measurement arm) may be further performed.

(S2: Acquire Cross Sectional Image)

Upon completion of the alignment in step S1, the ophthalmic apparatus 1 acquires a cross sectional image by applying OCT to the fundus Ef. This process includes: a scanning step of applying an OCT scan of a predetermined scan mode to the fundus Ef; and an image constructing step of constructing a cross sectional image from the data acquired by the OCT scan. The scanning step is executed by the main controller 211 by controlling the OCT unit 100, the optical scanner 44, and other elements.

The scan mode applied to the OCT scan is, for example, a B-scan that passes through a region of the fundus Ef to which a three dimensional OCT scan is to be applied in the subsequent step S6. As an example, when the application area of the three dimensional OCT scan is a region of 6 mm×6 mm area centering on the fovea centralis, the location of the B-scan can be set so as to pass through the center position of the region. Further, the number of B-scans may be any number equal to one or larger. For example, a horizontal scan (a B-scan along the x direction) and a vertical scan (a B-scan along the y direction), each of which passes through the center position of the application area of the three dimensional OCT scan, can be performed. This means that the scan mode may be a cross scan.

It should be noted that the scan mode applied to the OCT scan in step S2 is not limited to a B-scan or a combination of two or more B-scans. For example, any scan mode such as a circle scan or a three dimensional scan can be applied to the OCT scan in step S2.

(S3: Is this Good Cross Sectional Image?)

The ophthalmic apparatus 1 (for example, the data processor 230) determines whether or not a good cross sectional image has been acquired in step S2. This determination process may include, for example, at least the determination of the position of the image of the predetermined tissue of the fundus Ef in the frame (in particular, the position in the z direction), and may further include the determination of the interference intensity, the determination of the image quality, or other kinds of determination. The predetermined tissue subject to the position determination is, for example, the surface of the fundus Ef (i.e., the inner limiting membrane). The determination processes may be carried out in the same manner as conventional determinations.

When it is determined that a good cross sectional image has not been acquired (S3: No), the process proceeds to step S4. On the other hand, when it is determined that a good cross sectional image has been acquired (S3: Yes), the process proceeds to step S6.

(S4: Correct Optical Path Length of Interference Optical System)

When it is determined in step S3 that a good cross sectional image has not been acquired (S3: No), the main controller 211 executes at least one of the optical path length correction for the measurement arm and the optical path length correction for the reference arm. The optical path length correction is executed so that an image of a predetermined tissue of the fundus Ef is depicted within a predetermined area of the frame.

The correction amount of the optical path length is calculated by the data processor 230, based on the positional relationship between the depicted position of the predetermined tissue of the fundus Ef and the predetermined area of the frame, for example. In other words, the correction amount corresponding to the deviation (shift) of the depicted position of the predetermined tissue of the fundus Ef with respect to the predetermined area of the frame is calculated.

The optical path length correction for the measurement arm is performed by the main controller 211 controlling the retroreflector driver 41A for moving the retroreflector 41. Further, the optical path length correction for the reference arm is performed by the main controller 211 controlling the retroreflector driver 114A for moving the retroreflector 114.

(S5: Adjust Focus of Interference Optical System)

Next, the main controller 211 performs focus adjustment of the measurement arm. The focus adjustment is performed using, for example, the abovementioned determination of the interference intensity, the abovementioned determination of the image quality, or another determination. The focus adjustment may be performed by using the split indicator.

When the optical path length correction and the focus adjustment of the interference optical system have been performed, the process returns to step S2 to acquire a new cross sectional image, and then the determination whether the new cross sectional image is good or not is performed. Steps S2 to S5 may be repeated until the determination result "Yes" is obtained in step S3. Note that it may be configured to output an imaging error when the number of repetitions of the steps has reached a predetermined number of times or when the execution time of the repetition reaches a predetermined time. When an imaging error has been output, for example, the ophthalmic apparatus 1 can perform the processing again from step S1 or shift to manual adjustment.

(S6: Perform Three Dimensional OCT)

When it is determined in step S3 that a good cross sectional image has been acquired (S3: Yes), the ophthalmic apparatus 1 applies the three dimensional OCT to the fundus Ef to acquire the three dimensional image data 500. This process includes: a scanning step of applying an OCT scan of a predetermined three dimensional scan mode (e.g., the raster scan) to the fundus Ef; and an image constructing step of constructing the three dimensional image data 500 from the three dimensional data acquired by the OCT scan.

(S7: Detect Optical Path Length of Interference Optical System)

The main controller 211 detects the optical path length of the interference optical system (the optical path length of the measurement arm, the optical path length of the reference arm) when the OCT scan has been applied in step S6.

When the optical path length of the measurement arm is variable, the optical path length of the measurement arm is determined based on the position of the retroreflector 41 when the OCT scan has been applied in step S6. Similarly, when the optical path length of the reference arm is variable, the optical path length of the reference arm is determined based on the position of the retroreflector 141 when the OCT scan has been applied in step S6. When the optical path length of the measurement arm (or the optical path length of the reference arm) is fixed, for example, the value of the fixed optical path length stored in advance in the storage 212 is referred to.

(S8: Obtain Working Distance Value)

Further, the main controller 211 obtains the value of the working distance when the OCT scan has been applied in step S6. In the present example, for example, the default value WD of the working distance stored in advance in the storage 212 is referred to.

(S9: Calculate Estimated Value of Axial Length)

The first calculator 2321 calculates an estimated axial length of the subject's eye E based on the optical path length of the measurement arm and the optical path length of the reference arm acquired in step S7 and the working distance value acquired in step S8.

(S10: Detect Position of Focusing Lens)

Further, the main controller 211 detects the position of the OCT focusing lens 43 when the OCT scan has been applied in step S6. When the movement of the OCT focusing lens 43, the movement of the photography focusing lens 31, and the movement of the focus optical system 60 are executed in an interlocking manner, the position of the OCT focusing lens 43 may be obtained from the position of the photography focusing lens 31 (or, from the position of the focus optical system 60).

The detection of the position of the OCT focusing lens 43 may be the detection of the position of the OCT focusing lens 43 itself or the detection of the operation state of the actuator of the OCT focus driver 43A. The same also applies to the detection of the position of the photography focusing lens 31 and the detection of the position of the focus optical system 60.

(S11: Calculate Estimated Value of Diopter)

The second calculator 2322 calculates an estimated value of the diopter of the subject's eye E based on the position information of the OCT focusing lens 43 acquired in step S10.

(S12: Calculate Magnification Correction Value)

The correction value calculator 232 calculates the magnification correction value based on the estimated value of the axial length calculated in step S9 and the estimated value of the diopter calculated in step S11.

(S13: Correct Size of Three Dimensional Image Data)

The magnification corrector 233 corrects the size of the three dimensional image data 500 constructed in step S6 based on the magnification correction value calculated in step S12.

(S14: Generate Layer Thickness Distribution Data)

The distribution data generator 231 generates the layer thickness distribution data (the distribution data 300) based on the three dimensional image data 500 whose size has been corrected in step S13.

(S15: Compare Layer Thickness Distribution Data with Normative Data)

The data comparator 234 compares the layer thickness distribution data 300 generated in step S14 and the normative data 400 with each other.

(S16: Display Comparison Map)

The main controller 211 generates a comparison map representing the comparison result obtained in step S15 and displays the comparison map on the display 241 (END).

Figure 7:
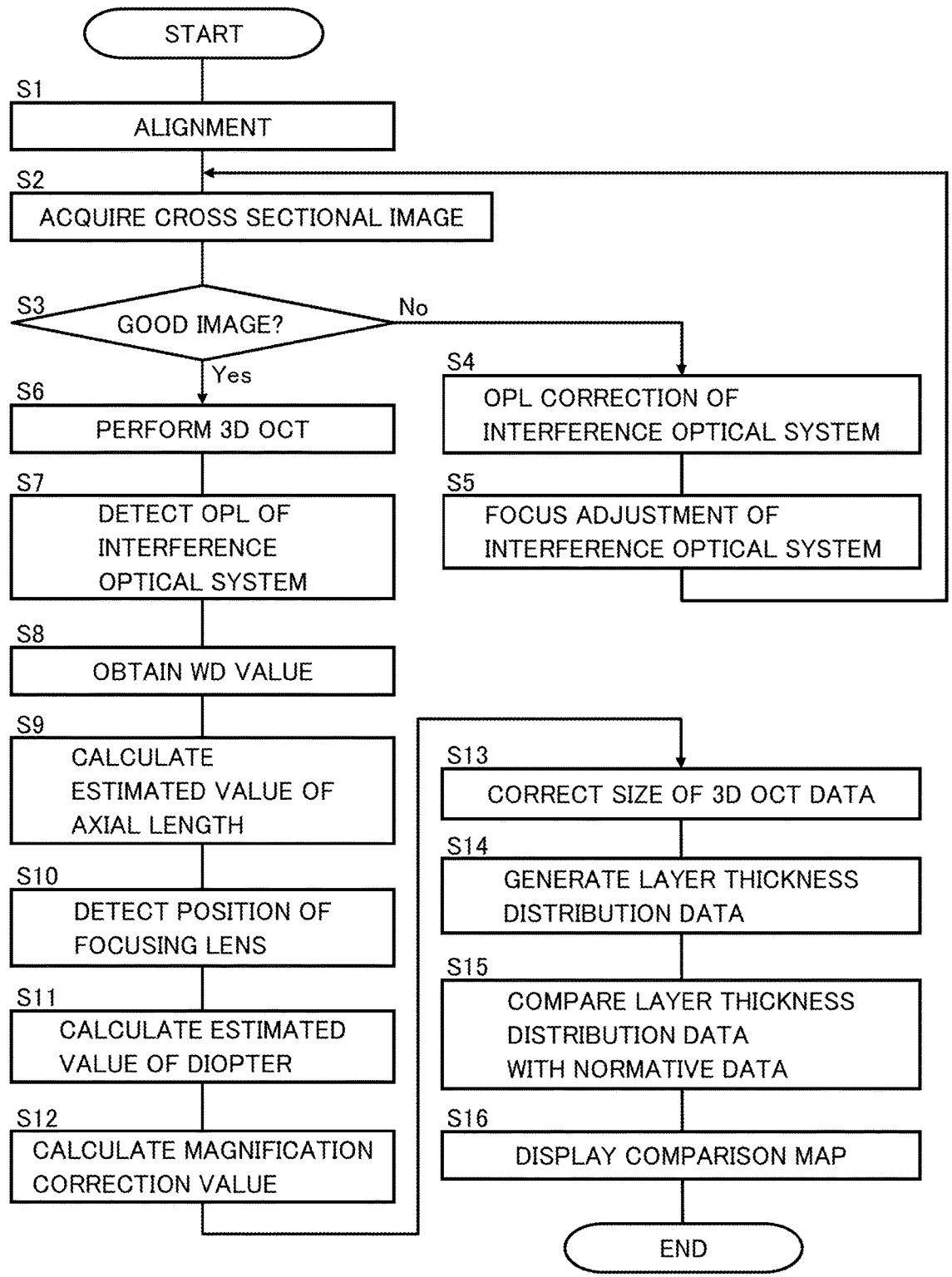
FIG. 7 is a flowchart illustrating an example of the operation of the ophthalmic apparatus according to the embodiment.

It should be noted that the operation example shown in FIG. 7 can be executed when the data processor 230 shown in FIG. 6B is employed. In contrast, when the data processor 230 shown in FIG. 6A is employed: the distribution data generator 231 generates the layer thickness distribution data 300 based on the three dimensional image data 500; the correction value calculator 232 calculates the magnification correction value; the magnification corrector 233 changes the size of at least one of the layer thickness distribution data 300 and the normative data 400 based on the magnification correction value to substantially equalize the size of the layer thickness distribution data 300 and the size of the normative data 400 with each other; the data comparator 234 executes the comparison between the layer thickness distribution data 300 and the normative data 400 whose sizes have been substantially equalized with each other; and the main controller 211 displays a comparison map representing the result of the comparison on the display 241.

MODIFICATION EXAMPLE

In the embodiment described above, the alignment is performed with referring to the alignment indicator image composed of two bright spot images, but the alignment method applicable to an ophthalmic apparatus is not limited thereto. In an ophthalmic apparatus that performs alignment of another method, the ophthalmic apparatus can calculate an estimated value of the axial length with a method according to the alignment of another method.

For example, there is an alignment method using a virtual image (Purkinje image) of a corneal reflection image formed by projecting a light beam onto the subject's eye (see, for example, Japanese Unexamined Patent Application Publication No. 2009-028287). In an ophthalmic apparatus that performs this alignment method, an estimated value of the axial length can be calculated with the position of the Purkinje image as a reference, that is, with the position of the cornea as a reference. For example, the first calculator 2321 can calculate an estimated value of the axial length of the subject's eye E, based on the relative position between the Purkinje image and the optical system after the alignment, the optical path length of the interference optical system (the optical path length of the measurement arm, the optical path length of the reference arm) when the three dimensional data of the fundus Ef is acquired, and a standard value of the corneal curvature radius set in advance.

When the alignment state is preferable, it is known that the position where the Purkinje image is formed is a position deviated from the corneal apex by a distance equal to half the corneal curvature radius in the intraocular direction. The working distance is acquired as the distance between the Purkinje image and the optical system (the objective lens 22). In the present example, the standard value of the corneal curvature radius (or the half value of the corneal curvature radius) is stored in advance in the storage 212. The standard value may be, for example, a clinically obtained statistical value or the value from the Gullstrand eye model.

Figure 8:
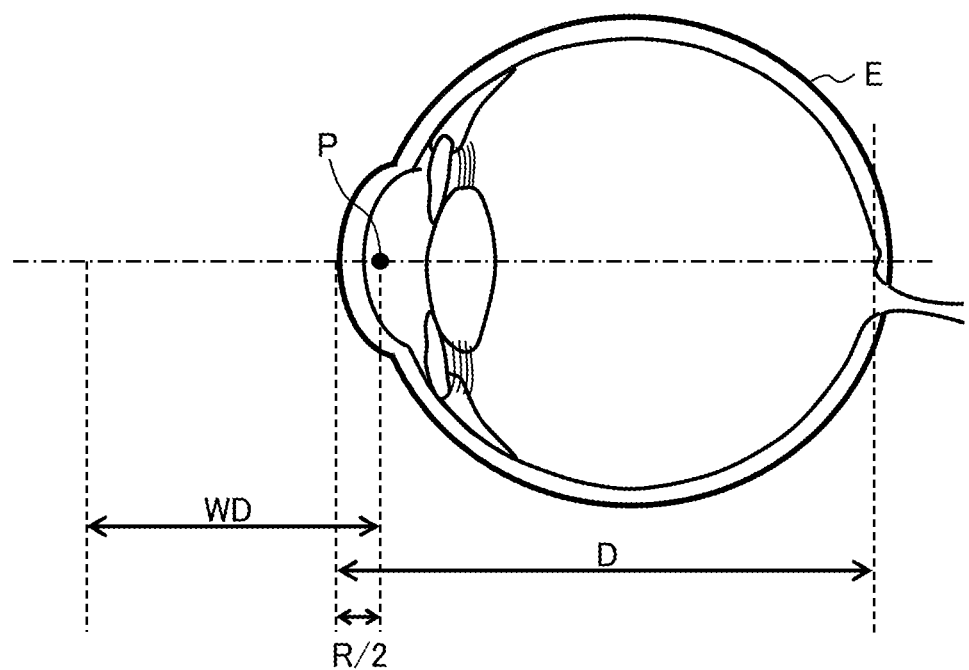
FIG. 8 is a schematic diagram for describing an example of processing executed by the ophthalmic apparatus according to the embodiment.

Given that the corneal curvature radius (the standard value thereof) is denoted by R, the optical path length of the reference arm is denoted by $OPL_R$, the optical path length of the measurement arm is denoted by $OPL_S$, the working distance is denoted by WD, and the intraocular distance between the position where the measurement light LS is incident on the subject's eye E and the position where the measurement light LS is reflected at the fundus Ef is denoted by D, there is the following relationship between these parameters: $OPL_R = OPL_S + WD + D - R/2$ (see FIG. 8). From this, the intraocular distance D (that is, the estimated value of the axial length D) can be expressed as follows: $D = OPL_R - OPL_S - WD + R/2$. It should be noted that the reference symbol P in FIG. 8 indicates the Purkinje image.

The first calculator 2321 can calculate the estimated value of the axial length D by substituting the corneal curvature radius R read out from the storage 212 in addition to the optical path length of the reference arm $OPL_R$, the optical path length of the measurement arm $OPL_S$, and the working distance WD each obtained in the same manner as in the above embodiment, into the above arithmetic formula "$D = OPL_R - OPL_S - WD + R/2$".

As another alignment method, there is an alignment method using two or more anterior eye segment images acquired by imaging the subject's eye E from different directions from each other (see, for example, Japanese Unexamined Patent Application Publication No. 2013-248376). In an ophthalmic apparatus that performs this alignment method, an estimated value of the axial length can be calculated with the position of a predetermined site of the anterior eye segment as a reference, for example, with the position of the pupil as a reference. For example, the first calculator 2321 can calculate an estimated value of the axial length of the subject's eye E, based on the relative position between the pupil of the subject's eye E and the optical system after the alignment, the optical path length of the interference optical system (the optical path length of the measurement arm, the optical path length of the reference arm) when the three dimensional data of the fundus Ef is acquired, a standard value of the corneal thickness set in advance, and a standard value of the anterior chamber depth set in advance.

According to this alignment method, for example, the optical axis of the optical system coincides with the pupil center (or the center of gravity of the pupil) of the subject's eye E in the xy direction, as well as the optical system is disposed so that the distance between the pupil center and the optical system (the objective lens 22) becomes equal to a predetermined working distance in the z direction. In the present example, the standard value of the corneal thickness and the standard value of the anterior chamber depth are stored in advance in the storage 212. These standard values may be, for example, clinically obtained statistical values or the values from the Gullstrand eye model.

Figure 9:
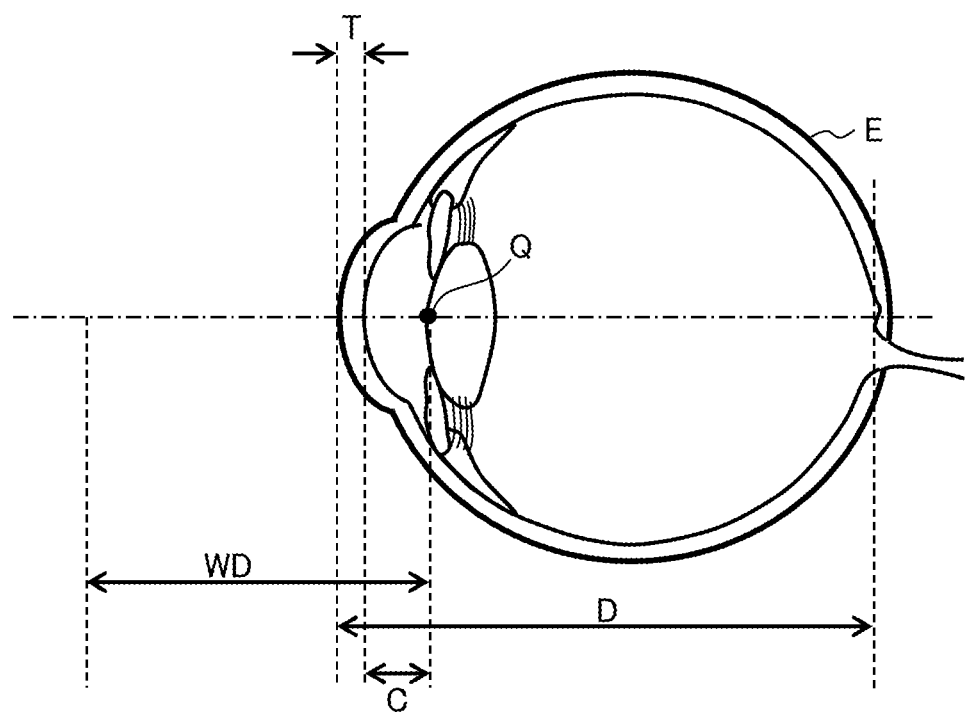
FIG. 9 is a schematic diagram for describing an example of processing executed by the ophthalmic apparatus according to the embodiment.

Given that the cornea thickness (the standard value thereof) is denoted by T, the anterior chamber depth (the standard value thereof) is denoted by C, the optical path length of the reference arm is denoted by $OPL_R$, the optical path length of the measurement arm is denoted by $OPL_S$, the working distance is denoted by WD, and the intraocular distance between the position where the measurement light LS is incident on the subject's eye E and the position where the measurement light LS is reflected at the fundus Ef is denoted by D, there is the following relationship between these parameters: $OPL_R = OPL_S + WD + D - T - C$ (see FIG. 9). From this, the intraocular distance D (that is, the estimated value of the axial length D) can be expressed as follows: $D = OPL_R - OPL_S - WD + T + C$. It should be noted that the reference symbol Q in FIG. 9 indicates the pupil center (or the center of gravity of the pupil).

The first calculator 2321 can calculate the estimated value of the axial length D by substituting the corneal thickness T and the anterior chamber depth C read out from the storage 212 in addition to the optical path length of the reference arm $OPL_R$, the optical path length of the measurement arm $OPL_S$, and the working distance WD each obtained in the same manner as in the above embodiment, into the above arithmetic formula "$D = OPL_R - OPL_S - WD + T + C$".

In the above embodiment, the estimated value of the diopter is determined based on the position of the OCT focusing lens 43 (or, based on information substantially equivalent the position of the OCT focusing lens 43), but a method applicable to an ophthalmic apparatus is not limited thereto. For example, an indicator image formed by projecting a light beam onto the fundus Ef can be detected, and an estimated value of the diopter can be calculated based on the indicator image detected.

The indicator image may be the split indicator image described above. As in a conventional case, the split indicator image is composed of two bright line images, and the relative position between the two bright line images changes according to the change in the focus state with respect to the fundus Ef. When a proper focus state is achieved, the two bright line images become to lie on the same straight line.

The two bright line images are detected by the photographing optical system 30 together with the observation image of the fundus Ef, for example. The second calculator 2322 extracts the two bright line images by analyzing the observation image and determines the relative position (the relative deviation direction, the relative deviation amount) between the two bright line images.

For example, relationship information indicating the relationship between relative positions between the two bright line images and values of the diopter is stored in advance in the storage 212. The values of the diopter recorded in the relationship information are, for example, defined as deviation amounts of the diopter with respect to a predetermined reference diopter. The reference diopter is, for example 0 diopter.

The second calculator 2332 obtains the value of the diopter corresponding to the relative position between the two bright line images extracted from the observation image, with referring to the relationship information described above. The value of the diopter can be used as the estimated value of the diopter of the subject's eye E.

Actions and Effects

Actions and effects of the ophthalmic apparatus according to the exemplary embodiment will be described.

The ophthalmic apparatus (1) of the present embodiment includes a data acquisition device, a distribution data generator, a correction value calculator, a magnification corrector, and a data comparator.

The data acquisition device is configured to acquire three dimensional data by applying optical coherence tomography (OCT) to the fundus of the subject's eye. Here, the type of the OCT scan mode is optional, and the raster scan is a typical example thereof.

In the configuration described in the present embodiment, the data acquisition device may include an element group for performing OCT. Specifically, the data acquisition device may include an element group disposed in the OCT unit 100, an element group that forms the measurement arm, and other element groups.

The distribution data generator is configured to generate distribution data of a predetermined measurement value in the eye fundus, based on the three dimensional data acquired by the data acquisition device. The type of the measurement value is optional, and typical examples thereof include the thickness of one or more predetermined tissues of the eye fundus, a blood flow parameter of eye fundus blood vessels (e.g., blood flow velocity, blood flow amount, etc.), the density of eye fundus blood vessels, and other kinds of measurement values.

In the configuration described in the present embodiment, the distribution data generator may include the followings: the image construction device 220 that constructs a plurality of pieces of cross sectional image data from the three dimensional data acquired by the data acquisition device; an element(s) in the data processor 230 that constructs three dimensional image data from the plurality of pieces of cross sectional image data; the distribution data generator 231 configured to generate distribution data from the three dimensional image data, and other elements.

The correction value calculator is configured to calculate a magnification correction value based on a predetermined condition for the data acquisition device to acquire the three dimensional data. The type of the condition is optional, and typical examples thereof include the condition related to alignment, the condition related to focus, the condition related to the optical path length of the OCT optical system (i.e., the interference optical system), and other types of conditions. Here, the condition related to the optical path length may include the optical path length of the measurement arm and the optical path length of the reference arm of the interference optical system. In the configuration described in the present embodiment, the correction value calculator may include the correction value calculator 232.

The magnification corrector is configured to change at least one of the size of standard distribution data generated in advance for the predetermined measurement value represented by the distribution data and the size of the distribution data, based on the magnification correction value calculated by the correction value calculator. Here, when changing the size of the distribution data, the size of the distribution data itself may be changed, or the size of any data from which the distribution data is generated may be corrected. Examples of the data from which the distribution data include three dimensional data, cross sectional image data and three dimensional image data. The type of the standard distribution data is optional, and typical examples thereof include the followings: normative data generated based on a sample of normal eyes (healthy eyes, healthy-seeming eyes); diseased eye data generated based on a sample of eyes diagnosed with a specific disease (e.g., data on highly myopic eyes, data on glaucomatous eyes, data on eyes with age-related macular degeneration, etc.); data generated based on a sample of eyes of persons having a specific attribute (e.g., age group, gender, race, medical history, etc.). In the configuration described in the present embodiment, the magnification corrector may include the magnification corrector 233.

The data comparator is configured to compare the standard distribution data and the distribution data with each other, at least one of whose sizes has been changed by the magnification corrector. Typically, the comparison processing includes a process of specifying data (standard measurement value) in the standard distribution data corresponding to each data (measurement value) in the distribution data, and a process of comparing the measurement value with the corresponding standard measurement value. In the configuration described in the present embodiment, the data comparator may include the data comparator 234.

According to the exemplary embodiment configured in this way, relative size adjustment (i.e., magnification correction) between the distribution data and the standard distribution data can be performed without having to refer to data acquired by another apparatus. Therefore, the present embodiment can be applied to screening examinations such as health check, unlike a conventional technique that requires data acquired by another apparatus to carry out the magnification correction. Further, the present embodiment can also be applied to examinations carried out at facilities that do not have an external device for acquiring the above data.

In the exemplary embodiment, the magnification correction value can be determined from an estimated value of the axial length of the subject's eye. In a typical example of the configuration applicable to that purpose, the correction value calculator may include a first calculator configured to calculate an estimated value of the axial length of the subject's eye based on the predetermined condition for the data acquisition device to acquire three dimensional data. Further, the magnification correction calculator may be configured to calculate the magnification correction value based on at least the estimated value of the axial length. Here, the estimated value of the axial length is a value obtained by an indirect measuring method rather than a value obtained by a method of directly measuring the axial length. The value obtained by the direct measuring method is, for example, a value acquired using an axial length measuring apparatus. In the configuration described in the present embodiment, the first calculator may include the first calculator 2321.

According to the exemplary configuration as described above, the magnification correction can be carried out using the estimated value of the axial length calculated based on the predetermined condition for the data acquisition device to acquire three dimensional data, without having to refer to the measurement value of the axial length of the subject's eye acquired by another apparatus.

Further, in the exemplary embodiment, the ophthalmic apparatus may include an alignment device for performing alignment of the data acquisition device with respect to the subject's eye. In addition, the data acquisition device may include the interference optical system and the optical path length changing device. As with a conventional OCT optical system, the interference optical system may be configured to split light from a light source into measurement light and reference light, project the measurement light onto the eye fundus, generate interference light by superposing the returning light of the measurement light from the subject's eye on the reference light, and detect the interference light. The optical path length changing device may be configured to change at least one of the optical path length of the measurement light and the optical path length of the reference light. In addition, the first calculator may be configured to calculate the estimated value of the axial length based on at least the result of the alignment, the optical path length of the measurement light, and the optical path length of the reference light. Here, the result of the alignment may be, for example, any parameter representing a state achieved through the alignment.

In the configuration described in the present embodiment, the alignment device may include the alignment optical system 50, the illumination optical system 10, and the photographing optical system 30. In addition, the interference optical system may include the followings: an element that splits the light from the light source unit 101 into the measurement light LS and the reference light LR (i.e., the fiber coupler 105); an element group configured to project the measurement light LS onto the fundus Ef (i.e., the element group forming the measurement arm); an element that generates the interference light LC by superposing the returning light of the measurement light LS from the subject's eye E on the reference light LR (i.e., the fiber coupler 122); and an element that detects the interference light LC (i.e., the detector 125).

According to the exemplary configuration as described above, the magnification correction can be carried out without having to refer to the measurement value of the axial length of the subject's eye acquired by another apparatus, since the ophthalmic apparatus 1 is configured to calculate the estimated value of the axial length of the subject's eye based on the condition related to alignment and the condition related to the OCT optical path length.

In the exemplary embodiment, the alignment device may be configured to perform the alignment based on a Purkinje image formed by projecting a light beam onto the subject's eye. Further, the first calculator may be configured to calculate the estimated value of the axial length of the subject's eye based on the relative position between the Purkinje image and the data acquisition device after the alignment, the optical path length of the measurement light and the optical path length of the reference light when the three dimensional data has been acquired by the data acquisition device, and a standard value of the corneal curvature radius set in advance.

Here, the relative position between the Purkinje image and the data acquisition device after the alignment may be, for example, any one of the followings: the relative position between the Purkinje image and the data acquisition device in a state achieved by the alignment using the Purkinje image; and the relative position between the Purkinje image and the data acquisition device when tracking is being performed to maintain the state achieved by the alignment using the Purkinje image. The standard value of the corneal curvature radius may be replaced by a half of the standard value of the corneal curvature radius. Further, the standard value may be, for example, a clinically obtained statistical value or a value from an eye model.

According to the exemplary configuration as described above, the ophthalmic apparatus 1 is configured to calculate the estimated value of the axial length of the subject's eye based on the condition related to the alignment on the basis of the Purkinje image (e.g., the working distance that is set to be the distance between the Purkinje image and the optical system), the condition related to the OCT optical path length, and the standard value of the corneal curvature radius. As a result of this, the magnification correction can be carried out without having to refer to the measurement value of the axial length of the subject's eye acquired by another apparatus.

In the exemplary embodiment, the alignment device may be configured to perform the alignment based on two or more anterior eye segment images acquired by photographing the subject's eye from mutually different directions. Further, the first calculator may be configured to calculate the estimated value of the axial length based on the relative position between the pupil of the subject's eye and the data acquisition device after the alignment, the optical path length of the measurement light and the optical path length of the reference light when the three dimensional data has been acquired, a standard value of the corneal thickness set in advance, and a standard value of the anterior chamber depth set in advance.

Here, the relative position between the pupil of the subject's eye and the data acquisition device after the alignment may be, for example, any of the followings: the relative position between the pupil and the data acquisition device in a state achieved by the alignment using the stereo imaging of the anterior eye segment; and the relative position between the pupil and the data acquisition device when tracking is being performed to maintain the state achieved by the alignment using the stereo imaging of the anterior eye segment. The standard value of the corneal thickness and the standard value of the anterior chamber depth may be, for example, a clinically obtained statistical value or a value from an eye model.

According to the exemplary configuration as described above, the ophthalmic apparatus 1 is configured to calculate the estimated value of the axial length of the subject's eye based on the condition related to the alignment using the stereo imaging of the anterior eye segment (e.g., the working distance that is set to be the distance between the pupil center and the optical system), the condition related to the OCT optical path length, the standard value of the corneal thickness and the standard value of the anterior chamber depth. As a result of this, the magnification correction can be carried out without having to refer to the measurement value of the axial length of the subject's eye acquired by another apparatus.

In the exemplary embodiment, the magnification correction value can be determined from the estimated value of the diopter of the subject's eye. In a typical example of the configuration applicable to that purpose, the correction value calculator may include a second calculator configured to calculate an estimated value of the diopter of the subject's eye based on the predetermined condition for the data acquisition device to acquire three dimensional data. Further, the correction value calculator may be configured to calculate the magnification correction value based on at least the estimated value of the diopter. Here, the estimated value of the diopter is a value obtained by an indirect measuring method rather than a value obtained by a method of directly measuring the diopter (i.e., the refractive power). The value obtained by the direct measuring method is, for example, a value acquired using a refractometer. In the configuration described in the present embodiment, the second calculator may include the second calculator 2322.

According to the exemplary configuration as described above, the magnification correction can be performed using the estimated value of the diopter calculated based on the predetermined condition for the data acquisition device to acquire three dimensional data, without having to refer to the measurement value of the diopter of the subject's eye acquired by another apparatus.

Further, in the exemplary embodiment, the data acquisition device may include the interference optical system described above. In addition, the ophthalmic apparatus may include a focus adjustment device for performing focus adjustment of the interference optical system. The second calculator may be configured to calculate the estimated value of the diopter of the subject's eye based on a focus state of the interference optical system. Here, the focus state of the interference optical system may be, for example, any parameter representing a state achieved by the focus adjustment. In the configuration described in the present embodiment, the focus adjustment device may include the focus optical system 60, the illumination optical system 10, and the photographing optical system 30.

According to the exemplary configuration as described above, the ophthalmic apparatus 1 is configured to calculate the estimated value of the diopter of the subject's eye based on the condition related to the focus. Therefore, the magnification correction can be carried out without having to refer to the measurement value of the diopter of the subject's eye acquired by another apparatus.

Further, in the exemplary embodiment, the focus adjustment device may include a focusing lens disposed in the optical path of the measurement light and a driver that moves the focusing lens along the optical path of the measurement light. In addition, the second calculator may be configured to calculate the estimated value of the diopter based on at least the position of the focusing lens in the optical path of the measurement light. In the configuration described in the present embodiment, the focusing lens is the OCT focusing lens 43, and the driver is the OCT focus driver 43A.

According to the exemplary configuration as described above, the ophthalmic apparatus 1 is configured to calculate the estimated value of the diopter of the subject's eye based on the position of the focusing lens that corresponds to the condition related to the focus. Therefore, the magnification correction can be carried out without having to refer to the measurement value of the diopter of the subject's eye acquired by another apparatus.

Also, in the exemplary embodiment, the focus adjustment device may be configured to detect an indicator image formed by projecting a light beam onto the eye fundus. In addition, the second calculator may be configured to calculate the estimated value of the diopter based on the indicator image detected. In the configuration described in the present embodiment, the indicator image is the split indicator image (i.e., the two bright line images).

According to the exemplary configuration as described above, the ophthalmic apparatus 1 is configured to calculate the estimated value of the diopter of the subject's eye based on the detection result of the indicator image that corresponds to the condition related to the focus. As a result of this, the magnification correction can be carried out without having to refer to the measurement value of the diopter of the subject's eye acquired by another apparatus.

Other Embodiment Examples

Figure 10A:
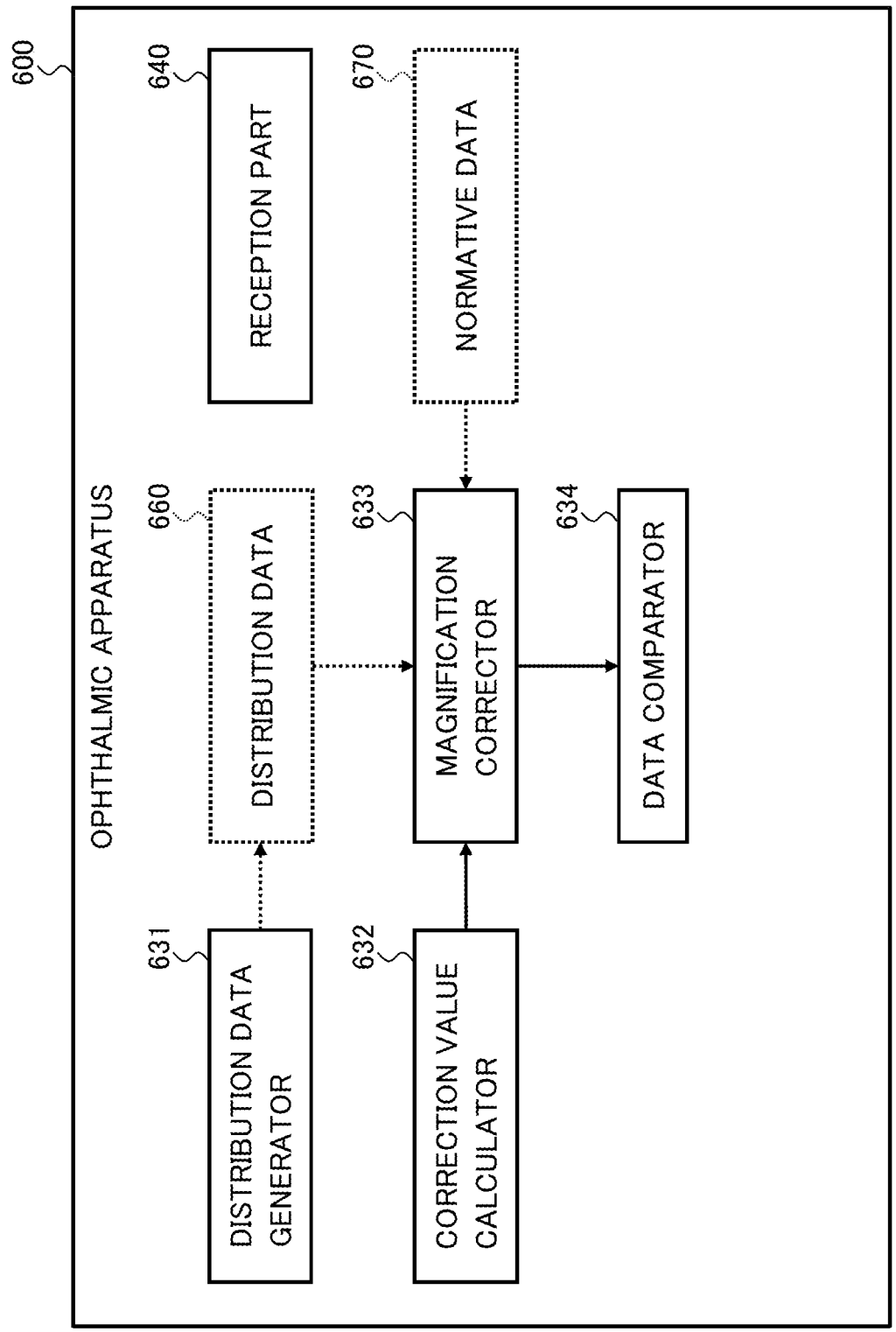
FIG. 10A is a schematic diagram illustrating an example of the configuration of the ophthalmic apparatus according to the embodiment.
Figure 10B:
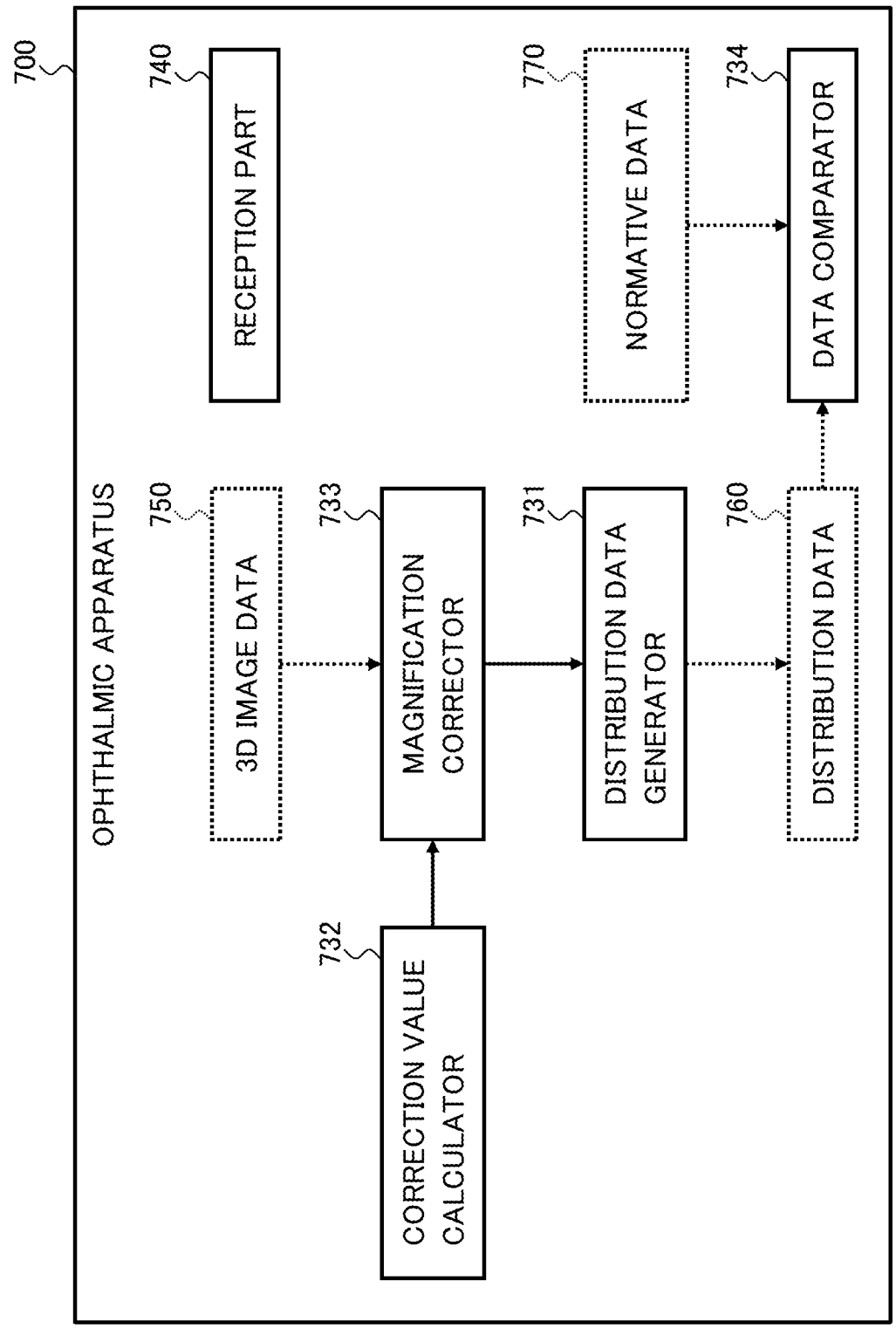
FIG. 10B is a schematic diagram illustrating an example of the configuration of the ophthalmic apparatus according to the embodiment.

In other embodiment examples, an ophthalmic apparatus may not have the OCT function. Such an ophthalmic apparatus includes at least a reception part for receiving data from outside and a processor for processing the data received. Specific examples thereof include a computer (information processing apparatus), an ophthalmic examination apparatus, an ophthalmic imaging apparatus, and other types of apparatuses. FIG. 10A, FIG. 10B, and FIG. 1 show examples of the configuration of such an ophthalmic apparatus.

The ophthalmic apparatus 600 shown in FIG. 10A includes the distribution data generator 631, the correction value calculator 632, the magnification corrector 633, the data comparator 634, and the reception part 640.

The reception part 640 receives three dimensional data acquired by applying OCT to the fundus of the subject's eye and a predetermined condition for acquiring the three dimensional data. The three dimensional data and the predetermined condition are obtained by, for example, an ophthalmic apparatus that has the OCT function similar to the ophthalmic apparatus 1 described above. Such an ophthalmic apparatus is hereinafter called an external ophthalmic apparatus. The ophthalmic apparatus 600 can accept the three dimensional data and the predetermined condition from the external ophthalmic apparatus, for example, via a communication line, a recording medium or another apparatus, or any combination of them.

The type of the communication line may be optional. For example, the communication line may include any one or more of a wired line, a wireless line, a dedicated line, the Internet, a WAN, a LAN, and other types of communication lines. In the case of acquiring data via a communication line, the reception part 640 includes a communication interface for performing data communication with an external device.

The type of the recording medium may be optional and may be any non-transitory recording medium such as a magnetic tape, a magnetic disk, an optical disk, a magneto-optical disk, a flash memory, a solid state drive, or another type of recording medium. In the case of acquiring data via a recording medium, the reception part 640 includes a device for reading data from the recording medium.

The distribution data generator 631 is configured to generate the distribution data 660 of a predetermined measurement value in the eye fundus based on the three dimensional data received by the reception part 640. The process is executed in the same manner as the distribution data generator 231 described above.

The correction value calculator 632 is configured to calculate the magnification correction value based on the predetermined condition received by the reception part 640. This process may be executed in the same manner as the correction value calculator 232 described above.

The magnification corrector 633 is configured to change at least one of the size of the distribution data 660 and the size of the standard distribution data (the normative data 670) generated in advance for the predetermined measurement value represented by the distribution data 660, based on the magnification correction value. This process may be executed in the same manner as the magnification corrector 233 described above.

The data comparator 634 is configured to compare the normative data 670 and the distribution data 660 with each other, at least one of whose sizes has been changed by the magnification corrector 633. This process may be executed in the same manner as the data comparator 234 described above.

According to the exemplary embodiment configured in this way, the magnification correction between the distribution data and the standard distribution data can be performed without having to refer to data acquired by another device or another apparatus.

Any items described above relating to the ophthalmic apparatus 1 can be combined with the ophthalmic apparatus 600 according to the present embodiment example.

The ophthalmic apparatus 700 shown in FIG. 10B includes the distribution data generator 731, the correction value calculator 732, the magnification corrector 733, the data comparator 734, and the reception part 740.

The reception part 740 is configured in the same way as the reception part 640 described above. The reception part 740 receives the three dimensional data 750 acquired by applying OCT to the fundus of the subject's eye and a predetermined condition for acquiring the three dimensional data 750.

The correction value calculator 732 is configured to calculate the magnification correction value based on the predetermined condition received by the reception part 740.

This process may be executed in the same manner as the correction value calculator 232 described above.

The magnification corrector 733 is configured to change the size of the three dimensional data 750 received by the reception part 740 based on the magnification correction value. This process may be executed in the same manner as the magnification corrector 233 described above.

The distribution data generator 731 is configured to generate the distribution data 760 of a predetermined measurement value in the eye fundus based on the three dimensional data 750 whose size has been changed by the magnification corrector 733. This process may be executed in the same manner as the distribution data generator 231 described above.

The data comparator 734 is configured to compare the distribution data 760 generated by the distribution data generator 731 and the standard distribution data (the normative data 770) generated in advance for the predetermined measurement value represented by the distribution data 760 with each other. This process may be executed in the same manner as the data comparator 234 described above.

According to the exemplary embodiment configured in this way, the magnification correction between the distribution data and the standard distribution data can be performed without having to refer to data acquired by another device or another apparatus.

Any items described above relating to the ophthalmic apparatus 1 can be combined with the ophthalmic apparatus 700 according to the present embodiment example.

A program according to the embodiment example makes a computer, which has received three dimensional data acquired by applying OCT to the fundus of the subject's eye and a predetermined condition for acquiring the three dimensional data, function as the distribution data generator 631 (731), the correction value calculator 632 (732), the magnification corrector 633 (733), and the data comparator 634 (734) as shown in FIG. 10A (or in FIG. 10B). Such a program can be stored in a non-transitory recording medium of any type.

Figure 11:
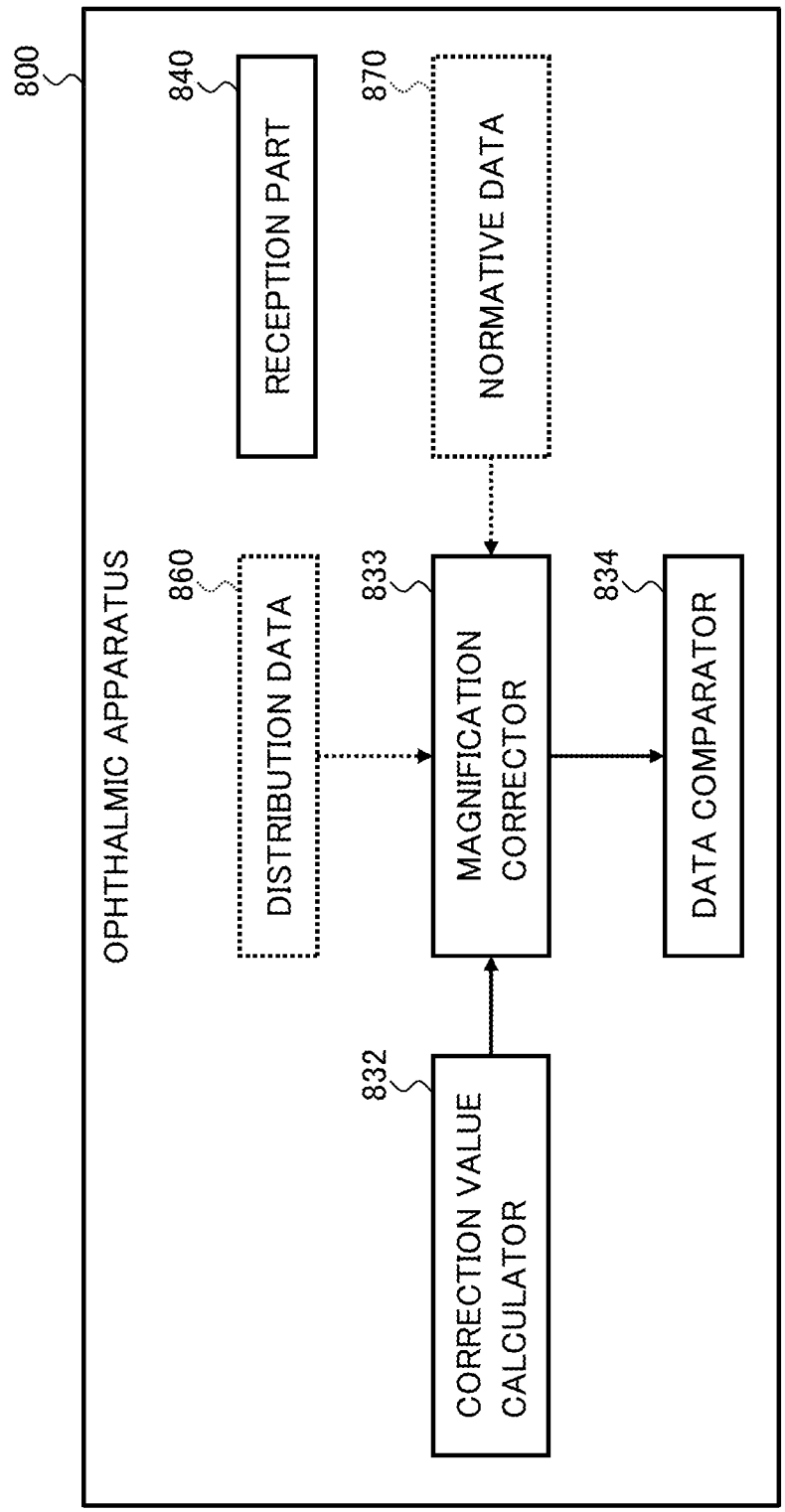
FIG. 11 is a schematic diagram illustrating an example of the configuration of the ophthalmic apparatus according to the embodiment.
Figure 12:
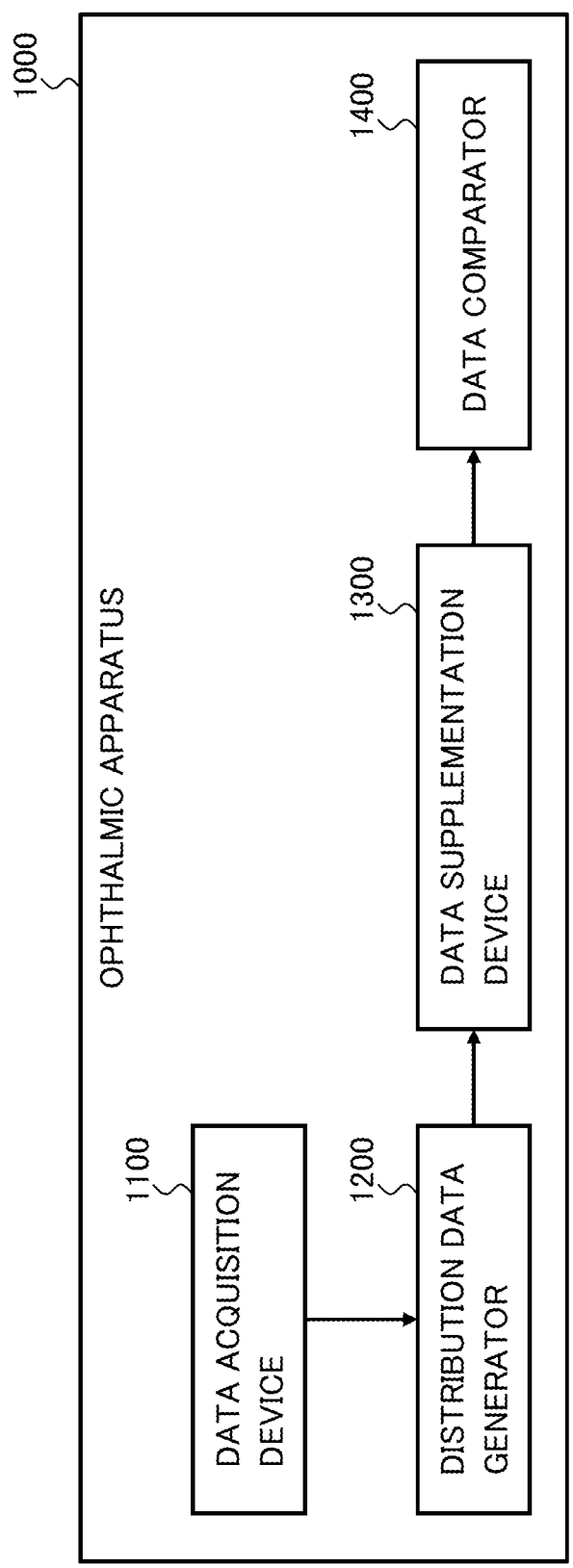
FIG. 12 is a schematic diagram illustrating an example of the configuration of the ophthalmic apparatus according to the embodiment.

The ophthalmic apparatus 800 shown in FIG. 11 includes the correction value calculator 832, the magnification corrector 833, the data comparator 834, and the reception part 840.

The reception part 840 receives the distribution data 860 of a predetermined measurement value in the eye fundus generated based on three dimensional data acquired by applying OCT to the fundus of the subject's eye and a predetermined condition for acquiring the three dimensional data. The reception part 840 is configured in the same way as the reception part 640 described above.

The correction value calculator 832 is configured to calculate the magnification correction value based on the predetermined condition received by the reception part 840. This process may be executed in the same manner as the correction value calculator 232 described above.

The magnification corrector 833 is configured to change at least one of the size of the distribution data 860 and the size of the standard distribution data (the normative data 870) generated in advance for the predetermined measurement value represented by the distribution data 860 received by the reception part 840, based on the magnification correction value. This process may be executed in the same manner as the magnification corrector 233 described above.

The data comparator 834 is configured to compare the normative data 870 and the distribution data 860 with each other, at least one of whose sizes has been changed by the magnification corrector 833. This process may be executed in the same manner as the data comparator 234 described above.

According to the exemplary embodiment configured in this way, the magnification correction between the distribution data and the standard distribution data can be carried out without having to refer to data acquired by another device or another apparatus.

Any items described above relating to the ophthalmic apparatus 1 can be combined with the ophthalmic apparatus 800 according to the present embodiment example.

A program according to the embodiment example makes a computer, which has received three dimensional data acquired by applying OCT to the eye fundus of the subject's eye and a predetermined condition for acquiring the three dimensional data, function as the correction value calculator 832, the magnification corrector 833, and the data comparator 834 as shown in FIG. 11. Such a program can be stored in a non-transitory recording medium of any type.

When both an external ophthalmic apparatus and the ophthalmic apparatus 600 (700) have the magnification correction function, information indicating whether or not the external ophthalmic apparatus has applied the magnification correction to three dimensional data can be input to the ophthalmic apparatus 600 (700). The information is attached to the three dimensional data and the predetermined condition, for example. When the magnification correction has already been performed by the external ophthalmic apparatus, the ophthalmic apparatus 600 (700) does not perform the magnification correction on the concerned three dimensional data or distribution data generated based thereon. Alternatively, the ophthalmic apparatus 600 (700) can check whether the magnification correction applied to the concerned three dimensional data by the external ophthalmic apparatus is appropriate. On the other hand, when the magnification correction has not been performed by the external ophthalmic apparatus, the ophthalmic apparatus 600 (700) performs the magnification correction on the concerned three dimensional data or distribution data generated based thereon.

Similarly, when both an external ophthalmic apparatus and the ophthalmic apparatus 800 have the magnification correction function, information indicating whether or not the external ophthalmic apparatus has applied the magnification correction to distribution data can be input to the ophthalmic apparatus 800. The information is attached to the distribution data and the predetermined condition, for example. When the magnification correction has already been performed by the external ophthalmic apparatus, the ophthalmic apparatus 800 does not perform the magnification correction on the concerned distribution data. Alternatively, the ophthalmic apparatus 800 can check whether the magnification correction applied to the concerned distribution data by the external ophthalmic apparatus is appropriate. On the other hand, when a magnification correction has not been performed by the external ophthalmic apparatus, the ophthalmic apparatus 800 performs the magnification correction on the concerned distribution data.

Second Embodiment

There are cases in which the magnification correction described in the first embodiment cannot cope with. Examples of such cases include a case where the area of the eye fundus represented by the distribution data is largely different from the definition area of the standard distribution data. The present embodiment can be employed for such cases, for example.

The ophthalmic apparatus 1000 according to the present embodiment includes the data acquisition device 1100, the distribution data generator 1200, the data supplementation device 1300, and the data comparator 1400.

The data acquisition device 1100 is configured to acquire three dimensional data by applying OCT to the fundus of the subject's eye. This process may be executed in the same manner as the data acquisition device of the ophthalmic apparatus 1 according to the first embodiment.

The distribution data generator 1200 is configured to generate distribution data of a predetermined measurement value in the eye fundus based on the three dimensional data acquired by the data acquisition device 1100. This process may be executed in the same manner as the distribution data generator 231 in the first embodiment.

When the distribution data does not include data corresponding to part of standard distribution data generated in advance for the predetermined measurement value indicated by the distribution data, the data supplementation device 1300 supplements the distribution data based on predetermined information. In a typical example, the predetermined measurement value is the layer thickness value of the eye fundus, the distribution data is the layer thickness distribution data, and the standard distribution data is the normative data of the layer thickness.

The determination whether or not the distribution data includes data corresponding to part of the standard distribution data can be executed by any processing using any parameter. For example, there is a case in which the axial length of the subject's eye is very short, and the area represented by distribution data is substantially smaller than the definition area of standard distribution data. Considering such a case, the ophthalmic apparatus 1000 may be configured to compare a measurement value of the axial length obtained in advance for the subject's eye and a predetermined threshold value with each other, and perform supplementation processing when the measurement value of the axial length is equal to or smaller than the predetermined threshold value. Alternatively, the ophthalmic apparatus 1000 may be configured to compare an estimated value of the axial length obtained in the same manner as in the first embodiment and a predetermined threshold value with each other, and perform supplementation processing when the estimated value of the axial length is equal to or smaller than the predetermined threshold value. Note that supplementation processing can also be applied to a case of requiring to acquire a measurement value for a location outside the area to which the OCT scan has been applied.

Examples of the supplementation processing will be described. In one example, the supplementation processing is executed using an arithmetic formula generated in advance based on clinical data or anatomical data. This arithmetic formula is defined, for example, using one or more parameters of any types as a variable(s). Examples of the parameters include the followings: a value of the axial length; a value of the diopter; a distance from a predetermined site of the eye fundus (e.g., from the fovea centralis or the optic nerve head); a direction to a predetermined site of the eye fundus; and a shape of the eye fundus (e.g., the curvature or bend of the surface of the eye fundus, the shape of a predetermined tissue). Further, the arithmetic formula may include one or more coefficients calculated based on clinical data or anatomical data.

The data supplementation device 1300 determines a value for each of one or more parameters set in advance, for example, based on any of the followings: data obtained by an examination performed in advance on the subject's eye (e.g., measurement data, imaging data, analytical data); a predetermined condition for acquiring three dimensional data; and a predetermined condition for acquiring image data. Then, the data supplementation device 1300 sets one or more parameter values determined to be a variable(s) of the arithmetic formula mentioned above. The data supplementation device 1300 can calculate a measurement value for a position outside the area to which the OCT scan has been applied, from the above arithmetic formula into which one or more parameter values have been substituted.

Another example of processing that can be executed by the data supplementation device 1300 will be described. In the present example, an artificial intelligence technique is used. The data supplementation device 1300 of the present example includes, for example, a knowledge acquisition processor and an inference processor. It should be noted that the knowledge acquisition processor may be provided in an external computer.

Any one or both of the knowledge acquisition processor and the inference processor can process, for example, a large number of pieces of distribution data, a large number of pieces of image data, a large number of pieces of analysis data, and other information (e.g., any medical information such as subject information, electronic medical record information, interpretation report, etc.), that have been acquired using the ophthalmic apparatus 1000 and/or other ophthalmic apparatuses.

The knowledge acquisition processor is configured to acquire knowledge by executing at least one of machine learning and data mining based on data collected in advance. The knowledge to be acquired includes knowledge about the distribution of a predetermined measurement value on the eye fundus (e.g., the layer thickness value).

The data used for machine learning and/or data mining may include any medical knowledge, knowledge about other academic fields, knowledge about any fields other than academic fields. Such knowledge may include, for example, any of the followings: knowledge based on specialized books (e.g., medical books); knowledge based on articles (e.g., medical treatises); knowledge based on information generated by public organizations or private organizations (e.g., clinical practice guidelines); knowledge based on dictionary (e.g., medical dictionary); knowledge based on corpus (e.g. medical corpus); knowledge based on knowledge base (e.g., medical knowledge base); knowledge obtained by other machine learning; knowledge obtained by other data mining; knowledge obtained by information and/or method other than the above knowledge items; and knowledge obtained from any combination of two or more of the above knowledge items.

Also, the data used for machine learning and/or data mining may include information and data used to obtain the knowledge of the types described above. For example, the data used for machine learning and/or data mining may include medical books, medical treatises, clinical practice guidelines, medical dictionaries, medical corpora, medical knowledge bases, data sets for machine learning (e.g., learning data, training data), data sets for data mining (e.g., big data), or other types of data and/or information.

Note that the knowledge includes, for example, information that can be recognized and explicitly expressed, and includes at least either one of empirical knowledge (e.g., knowledge acquired through experience or learning) and theoretical knowledge (e.g., theoretical background knowledge or system of specialized information). Typical examples of such knowledge include facts, rules, laws, judgment criteria, common sense, know-how, dictionaries, corpora, and others. In addition, the knowledge may include information relating to processing executed by an artificial intelligence processor (also referred to as an artificial intelligence engine or the like). For example, the knowledge may include weight parameters and bias parameters used in a neural network.

In machine learning, by analyzing the data collected as described above (mainly in a statistical manner), the knowledge acquisition processor extracts laws, rules, knowledge representations, judgment criteria, etc. from the data analyzed, and develop an algorithm of inference (described later) based on the information extracted.

The machine learning algorithm applicable to the knowledge acquisition processor is optional. Supervised learning, unsupervised learning, semi supervised learning, transduction, and multitasking learning are examples of the machine learning algorithm. In addition, examples of techniques applicable to machine learning executed by the knowledge acquisition processor include decision tree learning, association rule learning, neural network, genetic programming, inductive logic programming, support vector machine, clustering, Bayesian network, reinforcement learning, feature learning, and other techniques.

In data mining, the knowledge acquisition processor acquires knowledge by applying, to the data as described above, data analysis techniques such as statistics, pattern recognition, artificial intelligence, or other techniques.

Frequent pattern extraction, classification, regression analysis, and clustering are examples of analysis methods applicable to data mining executed by the knowledge acquisition processor.

The knowledge acquisition processor may be capable of executing any image processing and any analysis processing. Examples of the image processing include image enlargement, image reduction, image compression, image decompression, image rotation, binarization, gray scale representation, pseudo-color representation, contrast adjustment, smoothing, histogram, color information extraction, gamma correction, color correction, contour extraction (edge detection), noise removal, size measurement, feature extraction, pattern recognition, rendering, cross section conversion, and characteristic map creation. Examples of the analysis processing include segmentation, specification of an image region corresponding to a predetermined tissue, calculation of a thickness of a predetermined tissue (layer thickness value), derivation of a relationship between positions of an eye fundus and layer thickness values, derivation of relationships between a plurality of layer thickness values at a plurality of positions of an eye fundus.

In the present embodiment, the knowledge acquisition processor can execute at least one of the machine learning and the data mining based at least on the three dimensional image data of the eye fundus acquired by an OCT apparatus.

The knowledge acquired by the knowledge acquisition processor is stored in a predetermined storage device. The storage device may store not only the knowledge acquired by the knowledge acquisition processor but also the above-described various kinds of knowledge and data used in the knowledge acquisition processing.

For example, the inference processor draw inference based on any of the three dimensional data acquired by the data acquisition device 1100, the three dimensional image data constructed based on the three dimensional data, the distribution data generated based on the three dimensional image data, and based on the knowledge acquired by the knowledge acquisition processor.

The inference is a process of determining data not included in the distribution data. For example, the inference is a process of determining a predetermined measurement value (e.g., the layer thickness value) at a position outside the area of the eye fundus for which distribution data has been obtained, from the distribution data. Furthermore, the inference may be a process of determining a predetermined measurement value for a position that is outside the area of the eye fundus for which the distribution data has been obtained and is within the definition area of the standard distribution data, from the distribution data. By such inference, supplementation processing for the distribution data can be carried out. In other words, the estimation of measurement values can be realized for positions outside the area of the OCT scan for acquiring the distribution data. With this, distribution data corresponding to the entire definition area of the standard distribution data can be generated from distribution data only including data corresponding to part of the definition area of the standard distribution data, for example.

In the event that the knowledge acquisition processor is configured to perform machine learning, the inference processor can draw inference using an inference algorithm developed by the machine learning.

In the event that the knowledge acquisition processor is configured to perform data mining, the inference processor can draw inference using the knowledge acquired by the data mining.

In the event that the knowledge acquisition processor is configured to perform both machine learning and data mining, the inference processor can draw inference using at least one of an inference algorithm developed by the machine learning and the knowledge acquired by the data mining.

Note that the inference means to derive unknown information from known information, for example. Examples of the inference includes deduction, induction, abduction, complete knowledge based inference or reasoning, incomplete knowledge based inference or reasoning, object knowledge level inference, meta knowledge level inference, and other types. The inference is drawn using medical knowledge, expertise in other fields, general knowledge, knowledge acquired using an artificial intelligence technology, or other types of knowledge.

The data comparator 1400 is configured to compare the distribution data supplemented by the data supplementation device 1300 and the standard distribution data with each other. This process may be executed in the same manner as the data comparator 234 in the first embodiment.

According to the exemplary embodiment configured as described above, normative data comparative analysis or other types of analysis can be performed after the application of the supplementation processing to the distribution data in the event that the processing according to the first embodiment cannot be successfully applied. Further, the supplementation processing can also be applied to the distribution data in the event of wanting to acquire a measurement value for a position to which the OCT scan has not been applied.

In another embodiment example, an ophthalmic apparatus may not have the OCT function. Such an ophthalmic apparatus at least includes a reception part that receives data from outside and a processor that processes the data received. Specific examples thereof include a computer (information processing apparatus), an ophthalmic examination apparatus, an ophthalmic imaging apparatus, and other types of apparatuses.

In one example of such an ophthalmic apparatus, the reception part receives three dimensional data acquired by applying OCT to the fundus of the subject's eye. The distribution data generator is configured to generate distribution data of a predetermined measurement value in the eye fundus based on the three dimensional data. When the distribution data does not include data corresponding to part of standard distribution data generated in advance for the predetermined measurement value represented by the distribution data, the data supplementation device supplements the distribution data based on predetermined information. The data comparator is configured to compare the distribution data after the supplementation and the standard distribution data with each other.

In the ophthalmic apparatus according to another example, the reception part receives distribution data of a predetermined measurement value in the fundus of a subject's eye, which is generated based on three dimensional data acquired by applying OCT to the eye fundus. When the distribution data does not include data corresponding to part of standard distribution data generated in advance for the predetermined measurement value represented by the distribution data, the data supplementation device supplements the distribution data based on predetermined information. The data comparator is configured to compare the distribution data after the supplementation and the standard distribution data with each other.

Any items described in the first embodiment can be combined with the ophthalmic apparatus according to the present embodiment.

A program that makes a computer to execute the processes according to the present embodiment can be constructed.

The program according to the first example makes a computer, which has received three dimensional data acquired by applying OCT to the fundus of the subject's eye, function as each of the following processors; a distribution data generator (distribution data generation processor) that generates distribution data of a predetermined measurement value in the eye fundus based on the three dimensional data; a data supplementation device (data supplementation processor) that supplements the distribution data based on predetermined information when the distribution data does not include data corresponding to part of the standard distribution data generated in advance for a predetermined measurement value represented by the distribution data; and a data comparator (data comparison processor) that compares the distribution data after the supplementation and the standard distribution data with each other.

The program according to the second example makes a computer, which has received distribution data of a predetermined measurement value in the eye fundus generated based on three dimensional data acquired by applying OCT to the fundus of the subject's eye, function as each of the following processors: a data supplementation device (data supplementation processor) that supplements the distribution data based on predetermined information when the distribution data does not include data corresponding to part of the standard distribution data generated in advance for a predetermined measurement value; and a data comparator (data comparison processor) that compares the distribution data after the supplementation and the standard distribution data with each other.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:
1. An ophthalmic apparatus comprising:
a data acquisition device that acquires three dimensional data by applying optical coherence tomography to a fundus of a subject's eye, the data acquisition device including
an interference optical system that splits light from a light source into measurement light and reference light, projects the measurement light onto the fundus, generates interference light by superposing returning light of the measurement light from the subject's eye on the reference light, and detects the interference light, and
an optical path length changing device that changes at least one of an optical path length of the measurement light and an optical path length of the reference light;
processing circuitry configured to operate to perform alignment of the data acquisition device with respect to the subject's eye based on two or more anterior eye segment images acquired by imaging the subject's eye from different directions from each other;
the processing circuitry further configured to generate distribution data of a predetermined measurement value in the fundus based on the three dimensional data;
the processing circuitry further configured to calculate an estimated value of axial length of the subject's eye based on a predetermined condition for acquiring the three dimensional data, a result of the alignment, the optical path length of the measurement light and the optical path length of the reference light when the three dimensional data has been acquired, a standard value of a corneal thickness set in advance, a standard value of anterior chamber depth set in advance, and a relative position between a pupil of the subject's eye and the data acquisition device after the alignment, and
the processing circuitry further configured to calculate a magnification correction value based on the predetermined condition for acquiring the three dimensional data and the estimated value of axial length of the subject's eye;
the processing circuitry further configured to change at least one of a size of standard distribution data generated in advance for the predetermined measurement value and a size of the distribution data, based on the magnification correction value; and
the processing circuitry further configured to compare the standard distribution data and the distribution data with each other, at least one of whose sizes has been changed by the processing circuitry.
2. The ophthalmic apparatus of claim 1, wherein
the processing circuitry is further configured to perform the alignment based on a Purkinje image formed by projecting a light beam onto the subject's eye, and the processing circuitry further calculates the estimated value of the axial length based on a relative position between the Purkinje image and the data acquisition device after the alignment, the optical path length of the measurement light and the optical path length of the reference light when the three dimensional data has been acquired, and a standard value of a corneal curvature radius set in advance.

3. The ophthalmic apparatus of claim 1, wherein the the processing circuitry is further configured to calculate an estimated value of diopter of the subject's eye based on the predetermined condition, and to calculate the magnification correction value based on at least the estimated value of the diopter.

4. The ophthalmic apparatus of claim 3, wherein
the ophthalmic apparatus further comprises a focus adjustment device for performing focus adjustment of the interference optical system, and
the processing circuitry is further configured to calculate the estimated value of the diopter based on a focus state of the interference optical system.

5. The ophthalmic apparatus of claim 4, wherein the focus adjustment device comprises:
a focusing lens disposed in an optical path of the measurement light; and
a driver that moves the focusing lens along the optical path of the measurement light, and
the processing circuitry is further configured to calculate the estimated value of the diopter based on at least a position of the focusing lens in the optical path of the measurement light.

6. The ophthalmic apparatus of claim 4, wherein
the focus adjustment device detects an indicator image formed by projecting a light beam onto the fundus, and
the processing circuitry is further configured to calculate the estimated value of the diopter based on the indicator image.

7. The ophthalmic apparatus of claim 1, wherein the processing circuitry is further configured to supplement the distribution data based on predetermined information when the distribution data does not comprise data corresponding to part of standard distribution data generated in advance for the predetermined measurement value; and
the processing circuitry is further configured to compare the distribution data after supplementation with the standard distribution data.

8. An ophthalmic apparatus comprising processing circuitry configured to:
receive three dimensional data acquired by applying optical coherence tomography to a fundus of a subject's eye and a predetermined condition for acquiring the three dimensional data;
generate distribution data of a predetermined measurement value in the fundus based on the three dimensional data;
calculate an estimated value of axial length of the subject's eye based on the predetermined condition for acquiring the three dimensional data, a result of the alignment, the optical path length of the measurement light and the optical path length of the reference light when the three dimensional data has been acquired, a standard value of a corneal thickness set in advance, a standard value of anterior chamber depth set in advance, and a relative position between a pupil of the subject's eye and the data acquisition device after the alignment;
calculate a magnification correction value based on the predetermined condition and the estimated value of axial length of the subject's eye;
change at least one of a size of standard distribution data generated in advance for the predetermined measurement value and a size of the distribution data, based on the magnification correction value; and
compare the standard distribution data and the distribution data with each other, at least one of whose sizes has been changed by the processing circuitry.

9. An ophthalmic apparatus comprising processing circuitry configured to:
receive distribution data, generated based on three dimensional data acquired by applying optical coherence tomography to a fundus of a subject's eye, of a predetermined measurement value in the fundus and a predetermined condition for acquiring the three dimensional data;
calculate an estimated value of axial length of the subject's eye based on the predetermined condition for acquiring the three dimensional data, a result of the alignment, the optical path length of the measurement light and the optical path length of the reference light when the three dimensional data has been acquired, a standard value of a corneal thickness set in advance, a standard value of anterior chamber depth set in advance, and a relative position between a pupil of the subject's eye and the data acquisition device after the alignment;
calculate a magnification correction value based on the predetermined condition and the estimated value of axial length of the subject's eye;
change at least one of a size of standard distribution data generated in advance for the predetermined measurement value and a size of the distribution data, based on the magnification correction value; and
compare the standard distribution data and the distribution data with each other, at least one of whose sizes has been changed by the processing circuitry.

10. A method of operating an ophthalmic apparatus, the method comprising:
receiving distribution data, generated based on three dimensional data acquired by applying optical coherence tomography to a fundus of a subject's eye, of a predetermined measurement value in the fundus and a predetermined condition for acquiring the three dimensional data;
calculating an estimated value of axial length of the subject's eye based on the predetermined condition for acquiring the three dimensional data, a result of the alignment, the optical path length of the measurement light and the optical path length of the reference light when the three dimensional data has been acquired, a standard value of a corneal thickness set in advance, a standard value of anterior chamber depth set in advance, and a relative position between a pupil of the subject's eye and the data acquisition device after the alignment;
calculating a magnification correction value based on the predetermined condition and the estimated value of axial length of the subject's eye;
changing at least one of a size of standard distribution data generated in advance for the predetermined measurement value and a size of the distribution data, based on the magnification correction value; and comparing the standard distribution data and the distribution data with each other, at least one of whose sizes has been changed by the processing circuitry.

\* \* \* \* \*